(12) United States Patent
Ford et al.

(10) Patent No.: US 11,961,371 B2
(45) Date of Patent: Apr. 16, 2024

(54) VIRTUAL GAMING SYSTEM, SERVER AND METHOD

(71) Applicant: Potent Systems, Inc., West Palm Beach, FL (US)

(72) Inventors: John J. Ford, West Palm Beach, FL (US); Jason E. King, North Vancouver (CA)

(73) Assignee: Potent Systems, Inc., West Palm Beach, FL (US)

( * ) Notice: Subject to any disclaimer, the term of this patent is extended or adjusted under 35 U.S.C. 154(b) by 0 days.

(21) Appl. No.: 17/471,567

(22) Filed: Sep. 10, 2021

(65) Prior Publication Data
US 2022/0076538 A1 Mar. 10, 2022

Related U.S. Application Data

(60) Provisional application No. 63/076,877, filed on Sep. 10, 2020.

(51) Int. Cl.
*G07F 17/32* (2006.01)

(52) U.S. Cl.
CPC ...... *G07F 17/3288* (2013.01); *G07F 17/3211* (2013.01); *G07F 17/3223* (2013.01)

(58) Field of Classification Search
CPC ............ G07F 17/3288; G07F 17/3211; G07F 17/3223
See application file for complete search history.

(56) References Cited

U.S. PATENT DOCUMENTS

| 5,795,226 A * | 8/1998 | Yi | A63F 9/0406 463/6 |
| 2002/0058548 A1 * | 5/2002 | Stronach | G06Q 50/34 463/6 |
| 2003/0078087 A1 * | 4/2003 | Kojima | G07F 17/3288 463/6 |
| 2004/0009812 A1 * | 1/2004 | Scott | G07F 17/3251 463/28 |

* cited by examiner

*Primary Examiner* — Kevin Y Kim
(74) *Attorney, Agent, or Firm* — Greenberg Traurig, LLP

(57) ABSTRACT

In some embodiments, the disclosure describes a virtual sports interactive simulation media that displays a simulation of competitive events the results of which correspond to actual real-world live events. In some embodiments, simulated avatars represent live event competitors, and the results of the simulated event correspond to the live event results. In some embodiments, the system displays a simulated competition that is different from the live competition. In some embodiments, the system simulates action and/or drama to hide the outcome of the live event until at least a portion of the simulation is complete. In some embodiments, the system selects live events based on when a user decides to play. In some embodiments, the system provides the user with wagering options for different games. In some embodiments, the outcomes of actual events are displayed in a variety of game packages.

19 Claims, 24 Drawing Sheets

Select Game Package

| 4 Plays | 12 Plays |
| --- | --- |
| No bonus plays | + 1 bonus play |
| $2 | $5 |

MOST POPULAR

| 28 Plays | 60 Plays |
| --- | --- |
| + 5 bonus plays | + 14 bonus plays |
| $10 | $20 |

SAVE MORE! MULTIPACK

Game Description

Here be dragons to be found, here be

VIRTUAL GAMING SYSTEM, SERVER AND METHOD

CROSS-REFERENCE TO RELATED APPLICATION

This application claims the benefit of priority from U.S. Provisional Application No. 63/076,877, filed Sep. 10, 2020, entitled "POTENT VIRTUAL GAMING SYSTEM," which is incorporated herein by reference in its entirety.

BACKGROUND

Wagering games have been around for longer than written history. Some fixed probability wagering games include game pieces such as dice or cards where combinations of the pieces have a fixed probability of occurring throughout the gameplay as they are immune from outside influence under normal circumstances.

Another type of wagering game involves betting on the outcome of live competitions. These live competitions usually involve humans, animals, objects, machines, or a combination thereof trying to be the first to complete a course or obtain the greatest number of points within a given time. The probable outcome of live competitions can be calculated based on a team and/or athlete's past performance, but variabilities caused by environment, injury and many other factors can change the chances of winning.

A third type of wagering game involves a computer simulation of a fixed probability game or a live competition. For a simulated fixed probability game, the computer randomly presents a combination of the game pieces, and bets are paid according to the particular rules of the game. Computer simulations of live events, such as football as a non-limiting example, generally requires that multiple individuals gather in a simulated environment and control computer avatars in a quest to gain the most points or finish the game the fastest.

While there is a multitude of games to choose from, some gambling enthusiasts prefer a certain type of game such as car racing or horse racing. However, the type of live competition that suits a gambler's interest may not have a corresponding live event at the time the gambler wants to play. While a computer simulation may allow for the creation of a similar environment, it does not allow for the gambler to experience the thrill and uncertainty of a live event. In addition, computer program outcomes can be manipulated without a user being aware whereas outright cheating in a live competition is more apparent.

Therefore, there is a need for a system that presents a user with a simulated environment that has been created to suit a gamblers interest but also includes the attributes and outcomes associated with a real and/or live event.

SUMMARY

In some embodiments, the virtual sport gaming real event simulation system described herein (hereafter: the "system") is directed to a virtual sports interactive simulation media that displays a simulation of real-world events the results of which correspond to actual live events. (herein the terms "live event," "real event," "real-world event," "real-life event" and/or the like are synonymous with each other, and any reference to the preceding includes, but is not limited to, competitions occurring in real-time, but can also include any past competitions that occurred in the physical or digital world unless otherwise explicitly stated). In some embodiments, the results of the real-world wagers (hereafter: "wagers") placed on the simulation are displayed to the user via a virtual sports or games interactive display after the user's interactive interactions have selected a team, player or other variable or outcome of their choice, but before the result of the live events are known.

In some embodiments, the system represents one or more live events in a computer simulation (hereafter: "simulation" and/or "virtual race"). In some embodiments, the simulation uses an avatar to represent on or more competitors in the live event. In some embodiments, the computer simulation is presented to the user as a different event type. As a non-limiting example, a horse race may be presented to a user as a car race according to some embodiments. In some embodiments, the system is configured to create an avatar (e.g., a car) in the simulated environment (e.g., racecar track) that represents a competitor (e.g., a horse, athlete, team) in the live event. As used herein, a competitor can be a living organism (e.g., a dog) or a non-living structure or object (e.g., a model car moving under the influence of gravity or other motive forces). In some embodiments, each number (e.g., identification number) associated with an avatar in the simulation is configured to correspond with a number associated with a competitor in the live event. In some embodiments, the system is configured to display the odds associated with a competitor as the odds associated with a respective avatar in the simulation. In some embodiments, wagering is only allowed before the live event has started. In some embodiments, the system is configured to accept wagers at one or more points of time before the completion of the live event. In some embodiments, after a wager is made, and the live event has completed, the user is presented with competitor results from the live race in the form of avatar results in the simulation. In some embodiments, the system is configured to pay and/or collect wagers based on the results of the live event.

In some embodiments, the details of a live event include one or more of odds, total participants, type of game, game location, team and/or athlete names, country, weather, injury reports, history and/or any publicly available information. In some embodiments, the system is configured to display one or more details to a user. In some embodiments, the system is configured to hide one or more details of one or more live events from the user. In some embodiments, hiding one or more details enables a random wagering environment.

In some embodiments, the system is configured to present the same avatar for different live event types. In some embodiments, different live event types can occur sequentially. In some embodiments, multiple rounds of the same simulation (e.g., a car race) can each be a representation of a different live event. As a non-limiting example, in some embodiments, the system is configured to present five avatars in the form of cars for a simulated circuit race with three rounds, where each avatar will place 1-5 in each round, where each place is given a corresponding number of points, and the winner of the circuit race is the car with the most points at the end of the third round. In some embodiments, the system is configured to select a different live event for each round and assign different competitors to each avatar. In a non-limiting example, in some embodiments, the system is configured to choose a horse race for round one, a dog race for round two, and a bike race for round three, although the system is configured to display any type of race or simulation.

In some embodiments, the races chosen are based on when the races will occur. In some embodiments, the system is configured to choose live events that are scheduled within a specified period of time from each other. In some embodiments, the live events are chosen at random. In some embodiments, this improves the gambling experience as the gambler does not have to research available live events, make a wager on each live event, and then wait for those live events to complete. In some embodiments, the system is configured to simulate each round as the events occur using the avatars and simulated environment and report the results of each round to the user after completion.

In some embodiments, the system is configured to present a different avatar and/or simulated environment for the same live event type. In some embodiments, multiple rounds of the same live event type (e.g., a horse race) can each be represented by a different simulation. As a non-limiting example, in some embodiments system is configured to present five avatars in the form of cars for a live event circuit race with three rounds, wherein each competitor will place 1-5 in each round, each place is given a corresponding number of points, and the winner of the circuit race is the competitor with the most points at the end of the third round. In some embodiments, the system is configured to select a different avatar and/or simulated environment for each round. In some embodiments, the avatar for each round is given the same number corresponding to the same competitor in a live event. As a non-limiting example of simulating events, in some embodiments, the system is configured to simulate a horse race for round one, a dog race for round two, and a bike race for round three, wherein all three simulated races are based on the results of a single live event, such as a golf match play competition, as a non-limiting example. In some embodiments, this improves the gambling experience as the gambler can remotely view a completion in any desired format desired when no video feed is available. In some embodiments, the system is configured to simulate each round as it occurs using the avatars and simulated environment and report each round to the user after completion and/or pay all bets accordingly.

In some embodiments, the system is configured to simulate one or more portions of a live event. In some embodiments, the system is configured to create a scenario where avatar relative positions change during the simulation. In some embodiments, the system is configured to display relative avatar position changes that reflect competitor position changes during the live event. In some embodiments, the system is configured to display the position changes during at least a portion of the live event. In some embodiments, the system is configured to display the position changes and/or the entire simulation after the completion of the live event.

In some embodiments, the system is configured to display relative avatar positions that do not reflect the actual competitor position during the live event. As a non-limiting example, if a user and/or the system chooses a horse race as the live event, and only the results are posted for the live event, the system is configured to select the position of each avatar such that the winner cannot be determined until after a percentage of the race has completed. In some embodiments, the percentage is between 50%-100%, wherein 100% represents a "photo-finish." In some embodiments, the percentage is between 80%-100%. In some embodiments, the system is configured to simulate conditions that cause a change in speed, time, efficiency, and/or position through simulated incidents, accidents, malfunctions, environmental factors, competitor aggression, and/or any other scenarios that can be contemplated and/or has occurred during a similar live event. In some embodiments, the system is configured to display an avatar that represents a winner in a completed live event in at least one losing position in the simulation until after a percentage of the race is completed.

In some embodiments, the avatars are numbered in order of the probability odds of winning. As a non-limiting example, in some embodiments, an avatar numbered 1 has the highest probability of winning. In some embodiments, an avatar numbered 2 has the second highest chances of winning, and so on. In some embodiments, the largest numbered avatar represents a unicorn bet, where the payout is higher than the actual odds associated with that competitor. In some embodiments, the largest numbered avatar has the corresponding odds associated with the competitor.

In some embodiments, the system includes an algorithm to provide virtual sports where the number of outcomes differs between the real-life and the virtual sports display. As a non-limiting example, in some embodiments, the system might assign an avatar entry #1 to a real horse race entry #2, and avatar entry #2 to a real horse race entry #3, an avatar entry #3 to a real horse race entry #4, an avatar entry #4 to a real horse race entry #5, an avatar entry #5 to a real horse race entry #6, and an avatar entry #6 to a real horse race entry #1. In some embodiments the outcome of the virtual race entries would then correspond to the outcome of the paired real live event entries. In a non-limiting example, if real horse entry #3 won, the outcome of the virtual race displayed to a user would be a win by avatar #2 according to some embodiments. In some embodiments, winning payouts from the live entry #3 would be paid to those who selected avatar #2.

DRAWING DESCRIPTION

DETAILED DESCRIPTION

Figure 1:
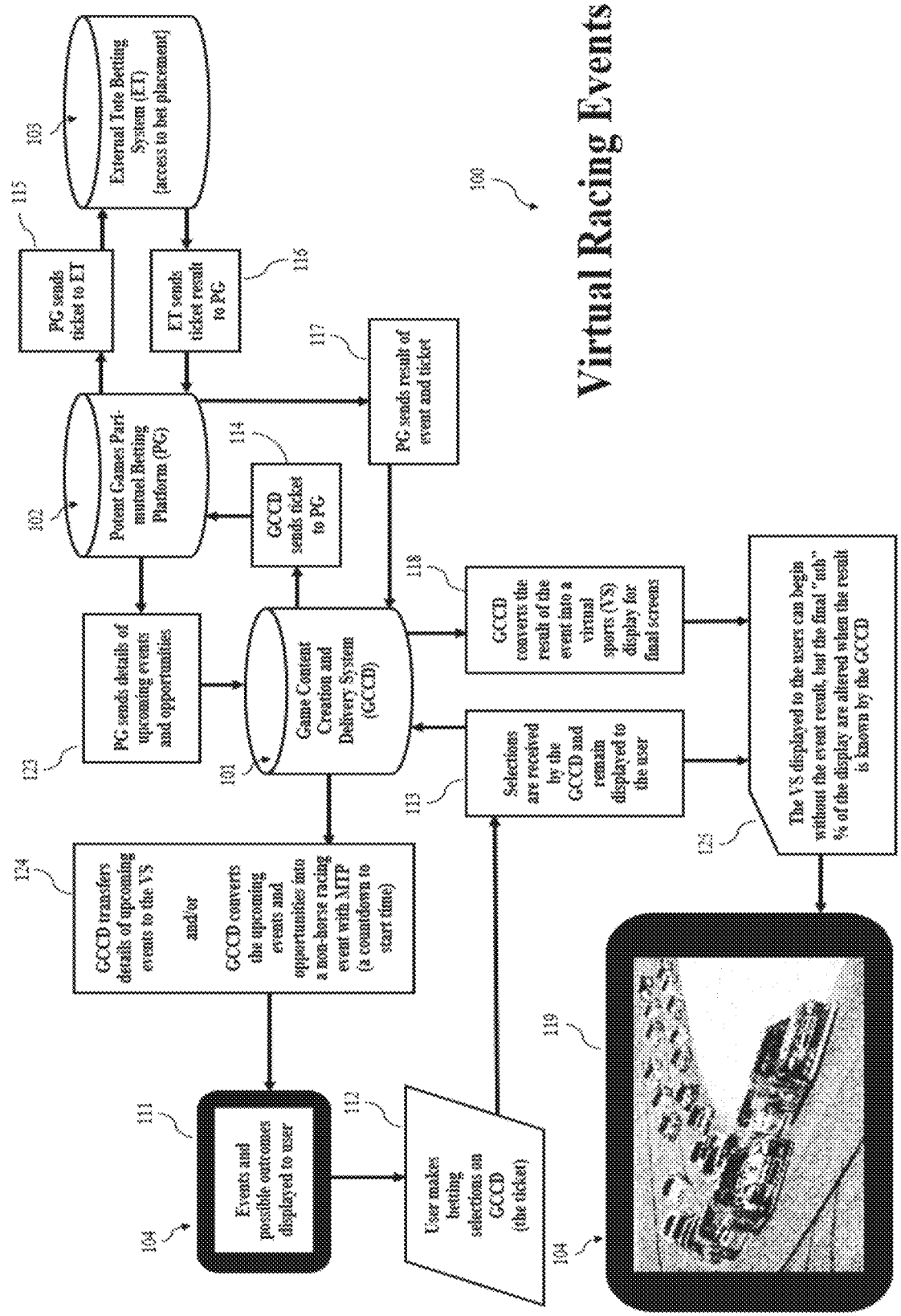
FIG. 1 is a flowchart illustrating the process flow executed by the system according to some embodiments.

In some embodiments, the system is directed to determining and/or displaying results in a virtual sports interactive simulation media (i.e., simulated events) based on, for example, real-world horse and greyhound events (i.e., real events). It is understood that specific names and events such as horse or car races are only used for descriptive purposes only, and can be replaced with more general descriptions such as a first avatar and a second (real) event when defining the metes and bounds of the system. In some embodiments, the outcomes are the same in the virtual sports interactive simulation as they are in the corresponding real-world horse and greyhound events. In some embodiments, the results of the real-world wagers are displayed to the user via a virtual sports or games interactive display after the user has interactively selected a team, player, or other competitor of their choice, but before the result of the live events are known.

As a non-limiting example, in some embodiments a 7-horse race represents a live event. In some embodiments, the system matches each horse to a like numbered car. In some embodiments, the system is configured to use that horse race to create a bike race, car race, etc. that represents a simulation of the horse race. In some embodiments, to keep from looking the same, can use horse number 1 to unicorn 4 for a unicorn race. In some embodiments, odds are displayed appropriately. In some embodiments, the system schedules the number scheme based on odds, but the system is also configured to apply randomly assigned numbers to at least one avatar according to some embodiments.

In some embodiments, when the results of the real-world wagers are known by the system, the system displays the same result as the real-world horse or greyhound event. In some embodiments, after the real-world event result is displayed to the user the user's selections on that live event are settled and any winnings due are paid to the user at the respective payoffs.

In some embodiments, the system is directed to a computer implemented method that includes one or more computers comprising one or more processors and one or more non-transitory computer readable media, the one or more non-transitory computer readable media including instructions stored thereon that configure the one or more computers to cause the one or more processors to execute and/or enable one or more of the following steps:

(1) receive, by the one or more processors, a request from a user to create a system account;

(2) map, by the one or more processors, one or more real events (e.g., a real horse or greyhound race) to one or more simulated races;

wherein, in some embodiments, the system is configured to display at least a portion of the mapping to the user;

wherein, in some embodiments, at least a portion of the mapping is not displayed to the user;

(3) generate, by the one or more processors, a lobby area comprising the one or more simulated events;

(4) display, by the one or more processors, the lobby area on a graphical user interface (GUI);

(5) receive, by the one or more processors, a user selection of at least one of the one or more simulated events;

(6) display, by the one or more processors, a selection of competitors and/or odds on the GUI;

wherein the odds and/or competitors are a replication of a real event which is currently taking place or about to start;

(7) display, by the one or more processors, real life pools as different branded "wagers" to the virtual sports user;

wherein, in some embodiments, the system is configured to and/or configured not to display one or more details about the simulated event;

(8) place, by the one or more processors, wagers and/or bets which replicate user selections into upcoming real events (e.g., real-world pari-mutuel pools on horse and/or greyhound live events);

(9) generate, by the one or more processors, the one or more active simulated events on the GUI;

wherein, in some embodiments, when the one or more active simulated events is displayed the result of the wagers and/or real events are unknown;

wherein, in some embodiments, during the one or more active simulated events the system is configured to display random competitor progress;

wherein, in some embodiments, the at least one simulated competitor's progress is randomized by the system for the first 80-90% of the one or more active simulated events;

wherein, in some embodiments, when one or more results of the real event is known by the system, the system is configured to alters the final 10%-20% the one or more active simulated events so that each of the results of the one or more active simulated events match the result of the real events; and wherein, in some embodiments, the system is configured to pay the user based on at least in part on the real wagers which have been placed.

In some embodiments, the system is configured to not begin an interactive display and/or simulation until the result of the wagers are known. In some embodiments, the simulated virtual sports event is an interactive display generated with the same number of real-life competitors (or outcomes) replicated with the same number of virtual sports simulated competitors (or outcomes).

In some embodiments, at the end of the active simulated event, the system is configured to update the user's account to reflect the result of the real event. In some embodiments, the system is configured to provide information to the user about the simulated event on which their selections were placed. In some embodiments, the system is configured to provide link to the real event in the display for the user to verify the results. In some embodiments, the information and/or link is provided in the transaction history.

FIG. 1 is a flowchart illustrating the process flow executed by the system for simulated events 100 (also referred to herein as virtual racing events) according to some embodiments. In some embodiments, the system includes one or more computers comprising one or more processors and one or more non-transitory computer readable media, the one or more non-transitory computer readable media including instructions stored thereon that configure the one or more computers to implement, execute, and/or enable one or more aspects of the system via the one or more processors. In some embodiments, the one or more processors are configured to implement one or more of a Game Content Creation and Delivery System module (GCCD; also referred to as a content module herein) 101, a Potent Games Pari-mutuel Betting Platform module (PG; also referred to as a platform betting module herein; although the module includes the name pari-mutuel, it is configured to place any type of bet) 102, an External Tote Betting System module (ET; also referred to as an external betting module herein) 103, and/or a Virtual Sports Display module (VS; also referred to as a display module herein) 104. In some embodiments, the system also includes one or more displays including one or more Graphical User Interfaces (GUIs) configured to display one or more aspects of the system including the VS 104. In some embodiments, one or more of the GCCD, PG, ET, VS and/or GUIs instructions are stored as modules on the one or more non-transitory computer readable media. It is understood that the names given to these modules are for descriptive purposes only and do not limit the functionality of the system in any way.

In some embodiments, shown as step 111, events and possible outcomes are displayed to the user by the system. In some embodiments, the PG 102 sends details of upcoming live events and betting opportunities to the GCCD at step 123. In some embodiments, the system is configured to transfer the details of the upcoming live events from the GCCD 101 to the VS 104 and display the details to the user on a display at step 124. In some embodiments, at step 112 the VS 104 is configured to enable a user to make one or more betting selections (all references to a "selection" and/or "selections" as used herein include one or more betting selections). In some embodiments, the GCCD is configured to create one or more tickets (all references to a "ticket" and/or "tickets" as used herein include one or more tickets) that include the selection at step 112. In some embodiments, the GCCD is configured to enable the user's selection and/or is configured to create the ticket at step 112. In some embodiments, the selection is received by the GCCD at step 113. In some embodiments, the selection and/or ticket remain displayed to the user at step 113 on the VS 104.

In some embodiments, at step 114 the GCCD sends the ticket to the Potent Games Pari-mutuel Betting Platform (PG) 102. In some embodiments, the PG then sends the ticket to the External Tote Betting System (ET) 103 at step 115. In some embodiments, the ET is configured to place one or more bets on one or more live events based on the ticket. In some embodiments, the ET is configured to receive the results of the one or more live events associated with the ticket.

In some embodiments, at step 116 the ET sends the ticket results to the PG. The PG then sends the results to the GCCD at step 117 according to some embodiments. In some embodiments, the GCCD then converts the result of the event on the ticket into one or more virtual races for display by the VS 104 at step 118. In some embodiments, at step 125 the system configures the VS 104 to display the virtual race (i.e., simulated event) 119 to the user.

In some embodiments, at step 124, the system is configured to allow the user to select a type of virtual race 119 and/or start the virtual race 119 before the ticket is sent to the PG at step 114. In some embodiments, at step 124, the system is configured to initiate the VS 104 including selecting the type of virtual race 119 and/or starting the virtual race 119 simultaneously and/or after the ticket is sent to the PG at step 114. In some embodiments, the virtual race 119 is a different type of race than the live event. In some embodiments, at step 125 the VS 104 displays the results of the virtual race 119 based on the live event is to the user ("user" or "users" as used herein include one or more users). In some embodiments, steps 124 and 125 are configured to overlap to some extent, where the VS 104 displayed to the user is configured to begin at step 124 without the system knowing the event results by randomizing one or more competitor's positions in the simulated event, but the a final percentage of the simulated event is altered to reflect one or more real competitor positions when the real event results are known by the GCCD at step 125.

In some embodiments, the system includes one or more sets of rules for the treatment of scratches. In some embodiments, pari-mutuel wagers are submitted by the system, but real competitors are subsequently scratched from the real event, meaning they won't participate in the event due to injury or disqualification. In some embodiments, in those occurrences, the racetrack will refund the wager amount back to the system. In some embodiments, instead of refunding these monies back to the user, the system is configured to include these monies when distributing other game winnings to the user, where one or more payouts include a winning amount and at least a portion of a refund amount. As a non-limiting example, if the system places 3 bets (e.g., win, place, show) in one or more races, and one or more horses are scratched from the one or more races, the system is configured to distribute the refunded amount from the scratched horses among the payouts from the one or more horses that completed the one or more races. In some embodiments, this improves customer experience by providing a winning experience versus receiving a notice of a cancelled wager and getting a refund.

In addition to racing style games, in some embodiments, the system is configured to enable a user to select one or more game package types as the medium to present winnings from real events. Various non-limiting examples of game packages the system supports include Scratch and Win game packages, Plinko game packages, Adventure Style game packages, Player Participant game packages, Arcade Style game packages, and Keno game packages according to some embodiments. In some embodiments, game packages are configured to provide a user a more interactive and/or prolonged experience with a selected game as opposed to being a spectator only (noting that some racing game embodiments do allow at least some control over an avatar during at least a portion of the race). In some embodiments, the system is configured to enable users to select one or more game packages at specified prices. In some embodiments, at least a portion of the funds used to purchase the game packages are then used to place wagers directly on real events and/or are placed in one or more player pools.

In some embodiments, the system includes one or more sets of rules for player pools. In some embodiments, as an alternative to submitting wagers for individual customers based on the purchase price of the individual's purchased game package, the system is configured to aggregate game package purchase prices from more than one customer and utilize the resulting total sum to submit a variety of pari-mutuel wagers. In some embodiments, the system is configured to distribute winnings from pari-mutuel wagers to customers in proportion to their respective game package purchase price.

In some embodiments, once a user purchases a game package, and/or the system's backend receives confirmation of the total value of the package, the system's algorithms then determine which upcoming race to wager on and/or the type of bets to place. In some embodiments, the type of bets to place are based on the bet types available for the race/races that can utilize all or a portion of the total wagered amount. In some embodiments, once the real race(s) have completed and the system has the results of the real race(s) (i.e., the total amount won and/or competitor placement), the system is configured to take the winnings and utilize a separate proprietary algorithm to determine the payout structure for the given game. In some embodiments, the system is configured to create a payout structure that divides the winnings between the number of available games in the given packages, and/or is configured to provide "weighting" for the potential payouts per game, in order to provide the ultimate "winning experience" for the user. In some embodiments, the system is configured to pay all funds from the winnings either out directly within the game, and/or in a subsequent "bonus" award at the end and/or after the game. In some embodiments, the system is configured to add monies not utilized for submitting wagers to the winnings amounts either within the game play and/or as a bonus award post playing of the game. In some embodiments, the system is configured to not add monies not utilized for submitting wagers to the winnings amounts either within the game play and/or as a bonus award post playing of the game.

In some embodiments, the system is directed to wagering algorithm strategies. In some embodiments, the system is configured to maximize payout to customers and/or maximize the frequency of winnings. In some embodiments, to maximize payout and/or frequency of winnings, the system is configured to determine and submit a series of pari-mutuel wagers from all or a portion of the purchase price of the game package selected by the user. In some embodiments, the wagers submitted will vary depending on the upcoming races and the wager types available in such races.

In some embodiments, the system is configured to adjust the wagering algorithms to modify the system's wagering models with the goal of maximizing payout and maximizing the frequency of winnings for the user. In some embodiments, the system is configured to examine the live odds to win (finishing first) and their corresponding payouts to find opportunities for larger or more frequent payouts.

In some embodiments, the system is configured to collect and utilize the following statistics:

Return to Player: In some embodiments, Return to Player is configured to be analyzed over time. In some embodiments, Return to Player is the percentage of all money wagered by players in a given period of time which is returned to them. As a non-limiting example, if $100 is wagered and $90 is paid back in winnings then the RTP is 90% according to some embodiments.

Max Win Multiple: In some embodiments, Max Win Multiple represents the current max multiple any customer has been paid out on their wagers. In some embodiments, Max Win Multiple is likely different for each different dollar amount paid for different game packages as the system will have more money to "risk" with the higher bet amounts.

Top Win Amount: In some embodiments, the system is configured to use Top Win Amount in marketing to promote the games.

Win Percentage Per Pack: In some embodiments, Win Percentage Per Pack represents how often a customer experienced a "winning experience" in any given package. In some embodiments, while a game package may have resulted in a net loss to the customer, the system is configured to monitor and maximize the impact of individual winning experiences in the games making up the game package.

In some embodiments, the system is configured to place wagers as close in time to the close of wagering as possible, so that the results of the wagers are available in as short of period of time as possible from the time the game package is purchased.

In some embodiments, the system is configured to place bets on Favorites. In some embodiments, placing a bet on the Favorite for Win, Place or Show—means the horse with the highest amount wagered on it (i.e., most popular) in the win, place, show pool totals. In some embodiments, if the system is placing a bet on the Favorite to Win, and a bet on the Favorite to Show, if the same horse is the favorite for both, then the system is configured to choose the next most popular horse to ensure not all the wagers are being put on one horse.

In some embodiments, the system provides wager distribution that are determined based on the game package purchase price. In some embodiments, some system wager distributions include:

$2 Game Package Amount

In some embodiments, the system is configured to offer the $2 Game Packages when there are upcoming races which offer $1 minimum bet type races. In some embodiments, $1 minimum bet type races extend the users interaction with the system by providing multiple opportunities to provide winnings for the customer.

In some embodiments, on a $2 Wager the system is configured to make two bets: a $1 Win Bet on the favorite; and a $1 Show Bet on the favorite. In some embodiments, if for some reason show wagering isn't available, then the system is configured to make the second wager a place bet on the favorite.

$10 Game Package Amount

In some embodiments, on a $1 or $2 wager minimum, the system is configured to make the following bets:
1) $5 Win Bet on the Favorite
2) $2 Place Bet on the Favorite for Second
3) $2 Show Bet on the Favorite for Third
4) $1 Exacta Bet on the Favorite for 1st/2nd (if available)

Figure 2:
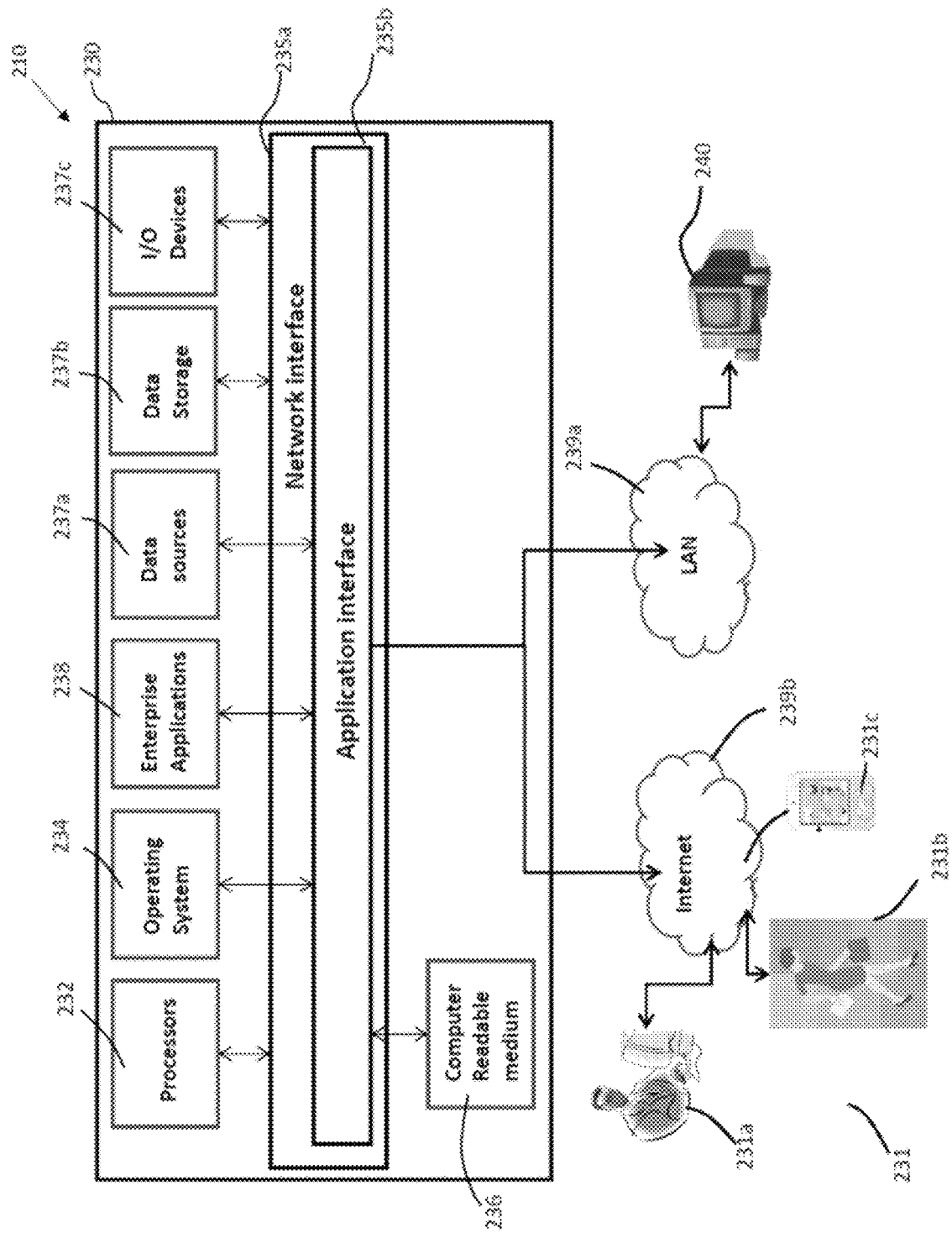
FIG. 2 is computer system including one or more processors and one or more non-transitory computer readable media suitable for executing the system according to some embodiments.

Or
1) $5 Win Bet on the Favorite
2) $3 Place Bet on the Favorite for Second
3) $2 Show bet on the favorite for Third
   or if not Show Bet
3) $2 Place bet on the favorite for Third
Or
1) $2 WPS on the Favorite ($6)
2) $2 on Favorite for 2nd to Place
3) $2 on the Favorite for 3rd to Show
$20 Game Package Amount In some embodiments, on a $1 or $2 wager minimum, the system is configured to make the following bets:
1) $5 WPS on the Favorite ($15)
2) $5 on Favorite for 2nd to Place
Or
1) $5 WPS on the Favorite ($15)
2) $3 on the Favorite for 2nd to Place
3) $2 on the Favorite for 3rd to Show
Or
1) $10 on the Favorite to Win
2) $10 on the Favorite for Second to Show FIG. 2 illustrates a computer system enabling and/or comprising the systems and methods described herein in accordance with some embodiments of the system. In some embodiments, the computer system 210 can include and/or operate and/or process computer-executable code and/or instructions of one or more of the above-mentioned software modules and/or systems. Further, in some embodiments, the computer system 210 can operate and/or display information within one or more graphical user interfaces. In some embodiments, the computer system 210 can comprise a cloud server and/or can be coupled to one or more cloud-based server systems.

In some embodiments, the system 210 can comprise at least one computing device including at least one processor 232. In some embodiments, the at least one processor 232 can include a processor residing in, or coupled to, one or more server platforms. In some embodiments, the system 210 can include a network interface 235a and an application interface 235b coupled to the least one processor 232 capable of processing at least one operating system 234. Further, in some embodiments, the interfaces 235a, 235b coupled to at least one processor 232 can be configured to process one or more of the software modules (e.g., such as enterprise applications 238). In some embodiments, the software modules 238 can include server-based software, and can operate to host at least one user account and/or at least one client account, and operating to transfer data between one or more of these accounts using the at least one processor 232.

With the above embodiments in mind, it is understood that the system can employ various computer-implemented operations involving data stored in computer systems. Moreover, the above-described databases and models described throughout can store analytical models and other data on computer-readable storage media within the system 210 and on computer-readable storage media coupled to the system 210. In addition, the above-described applications of the system can be stored on computer-readable storage media within the system 210 and on computer-readable storage media coupled to the system 210. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated. In some embodiments of the system, the system 210 can comprise at least one computer readable medium 236 coupled to at least one data source 237a, and/or at least one data storage device 237b, and/or at least one input/output device 237c. In some embodiments, the system can be embodied as computer readable code on a computer readable medium 236. In some embodiments, the computer readable medium 236 can be any data storage device that can store data, which can thereafter be read by a computer system (such as the system 210). In some embodiments, the computer readable medium 236 can be any physical or material medium that can be used to tangibly store the desired information or data or instructions and which can be accessed by a computer or processor 232. In some embodiments, the computer readable medium 236 can include hard drives, network attached storage (NAS), read-only memory, random-access memory, FLASH based memory, CD-ROMs, CD-Rs, CD-RWs, DVDs, magnetic tapes, other optical and non-optical data storage devices. In some embodiments, various other forms of computer-readable media 236 can transmit or carry instructions to a computer 240 and/or at least one user 231, including a router, private or public network, or other transmission device or channel, both wired and wireless. In some embodiments, the software modules 238 can be configured to send and receive data from a database (e.g., from a computer readable medium 236 including data sources 237a and data storage 237b that can comprise a database), and data can be received by the software modules 238 from at least one other source. In some embodiments, at least one of the software modules 238 can be configured within the system to output data to at least one user 231 via at least one graphical user interface rendered on at least one digital display.

In some embodiments of the system, the computer readable medium 236 can be distributed over a conventional computer network via the network interface 235a where the system embodied by the computer readable code can be stored and executed in a distributed fashion. As a non-limiting example, in some embodiments, one or more components of the system 210 can be coupled to send and/or receive data through a local area network ("LAN") 239a and/or an internet coupled network 239b (e.g., such as a wireless internet). In some further embodiments, the networks 239a, 239b can include wide area networks ("WAN"), direct connections (e.g., through a universal serial bus port), or other forms of computer-readable media 236, or any combination thereof.

In some embodiments, components of the networks 239a, 239b can include any number of user devices such as personal computers including for example desktop computers, and/or laptop computers, or any fixed, generally non-mobile internet appliances coupled through the LAN 239a. For example, some embodiments include personal computers 240a coupled through the LAN 239a that can be configured for any type of user including an administrator. Some embodiments can include personal computers coupled through network 239b. In some further embodiments, one or more components of the system 210 can be coupled to send or receive data through an internet network (e.g., such as network 239b). For example, some embodiments include at least one user 231 coupled wirelessly and accessing one or more software modules of the system including at least one enterprise application 238 via an input and output ("I/O") device 237c. In some other embodiments, the system 210 can enable at least one user 231 to be coupled to access enterprise applications 238 via an I/O device 237c through LAN 239a. In some embodiments, the user 231 can comprise a user 231*a* coupled to the system 210 using a desktop computer, and/or laptop computers, or any fixed, generally non-mobile internet appliances coupled through the internet 239*b*. In some further embodiments, the user 231 can comprise a mobile user 231*b* coupled to the system 210. In some embodiments, the user 231*b* can use any mobile computing device 231*c* to wireless coupled to the system 210, including, but not limited to, personal digital assistants, and/or cellular phones, mobile phones, or smart phones, and/or pagers, and/or digital tablets, and/or fixed or mobile internet appliances.

Figure 3:
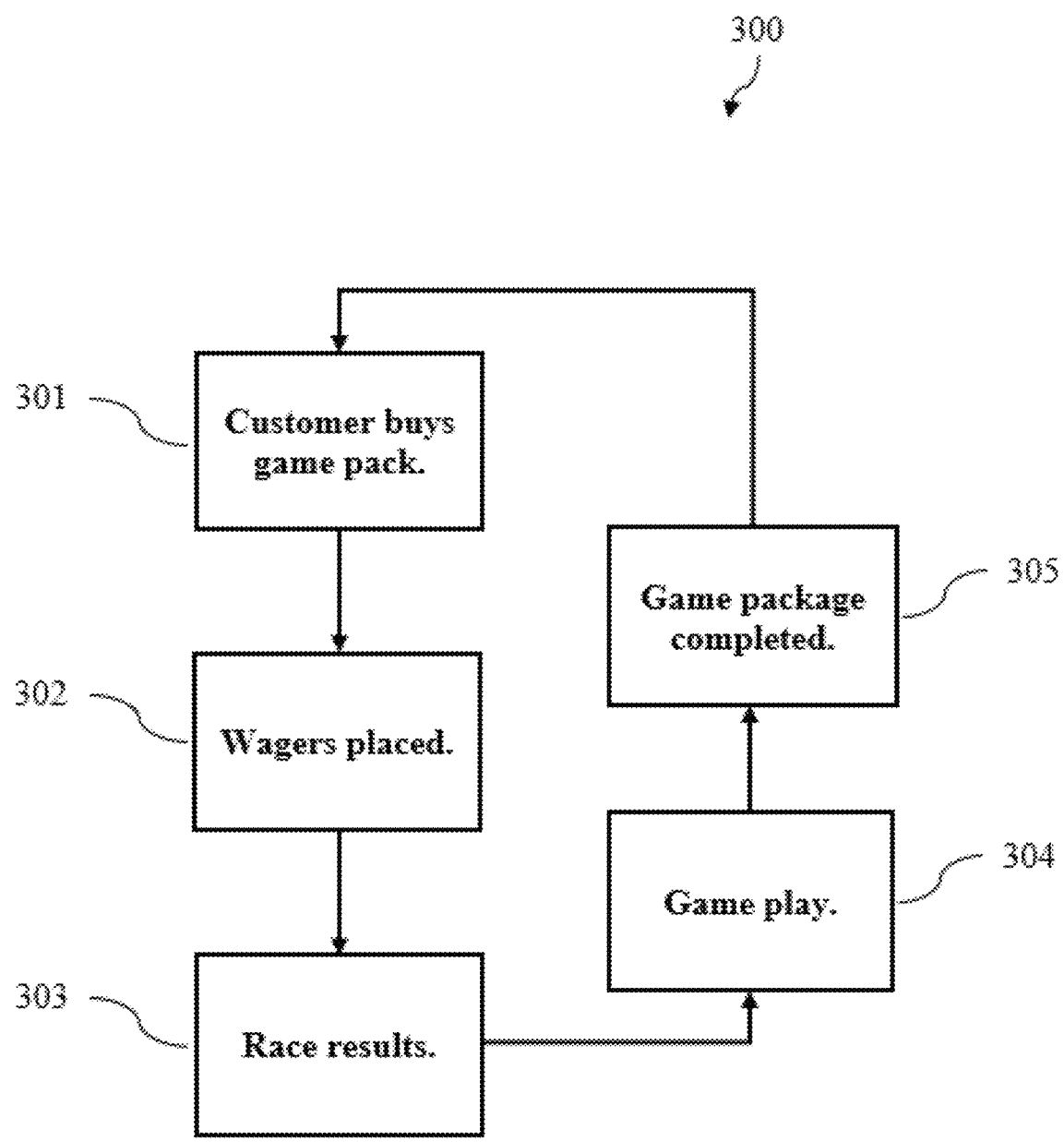
FIG. 3 shows a game play cycle according to some embodiments.

FIG. 3 shows a game play cycle 300 according to some embodiments. In some embodiments, the cycle begins at step 301 when a customer buys one or more game packs. In some embodiments, at step 301 the customer chooses a one or more games (e.g., Match 3, Slots, and/or Lottery) and chooses a package amount (e.g., $2-$50). In some embodiments, packages include one or more game rounds (e.g., 2 to 100).

In some embodiments, wagers are placed by the system at step 302. In some embodiments, at step 302 the system takes the funds from the game package purchase and algorithmically places wagers into the next available live race/event at one or more racetracks. In some embodiments, the system is configured to present a countdown to the customer as to when the game package will be available to play.

In some embodiments, the system receives the results of the live race at step 303. In some embodiments, when the live race ends the system is configured to receive the winnings from the wagers placed at the track and use those winnings to power the outcome of the game package. In some embodiments, the system is configured to notify the customer (e.g., visually and/or audibly) that the game package is available for play once the winning amounts are received. In some embodiments, the game package is available for play when a pre-determined percentage of the live event duration is complete before the outcome is known. In some embodiments, the pre-determined percentage includes an amount of time remaining in the (real event) live race that is less than the total duration of one or more virtual races.

The game play begins at step 304 according to some embodiments. In some embodiments, the customer begins playing the game package with each "game round" powered by the winning wagers from the live race results. In some embodiments, the system is configured to algorithmically divide the total winning wagers for one or more live races among the total game rounds in the package to produce the per round outcomes for the player/customer.

In some embodiments, at step 305 the game package is complete. In some embodiments, the system is configured to match the winnings from the original real event wagers and the total winnings from the game package once the customer completes the entire game package. In some embodiments, after step 305 is complete the system is configured to enable the customer to purchase another game package and the cycle begins again.

Figure 4:
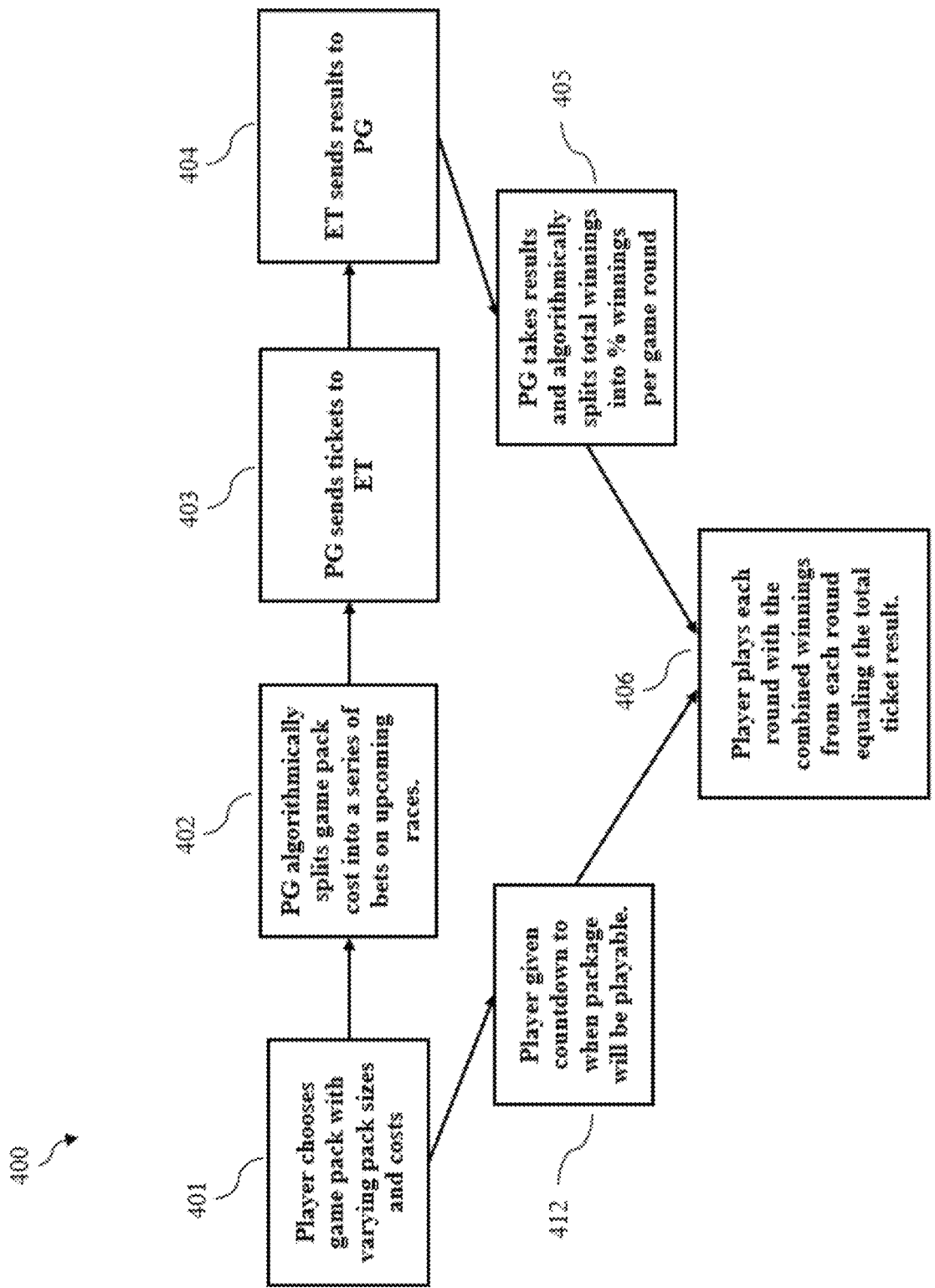
FIG. 4 shows a game architecture executed by the system according to some embodiments.

FIG. 4 shows a game architecture 400 executed by the system according to some embodiments. In some embodiments, at step 401 the player chooses one or more game packs with varying pack sizes and costs. In some embodiments, at step 402 the PG algorithmically splits game pack cost into a series of bets on upcoming live races. In some embodiments, at step 403 the PG sends the tickets to the ET where the ET makes the wagers on the one or more live races. In some embodiments, the ET sends the results of the one or more live events to the PG when the winners are determined at step 404. At step 405, the PG takes the results and algorithmically splits total winnings into a one or more percentage amounts, each percentage amount is presented to the user as winnings per game round as the user plays the virtual games according to some embodiments. In some embodiments, the player plays each round with the combined winnings from each round equaling the total ticket result at step 406. In some embodiments, after step 401 the player is given a countdown to when package will be playable at step 412, and the virtual game begins at step 406 with the countdown is complete.

In some embodiments, the system includes three primary types of games: type 1, type 2, and type 3 games. In some embodiments, the system is configured to enable a user to select one or more of a type 1, type 2, and type 3 game.

In some embodiments, type 1 games are configured to enable the user to specify one or more of a wager amount, a runner number, and a type of wager (e.g., to come in first, second or third, or some other finishing combination). In some embodiments, the system is configured to match a virtual racing game (i.e., simulated event) to a real-world live horse race (i.e., real event) for type 1 games. In some embodiments, the system is configured to mirror the odds from a living horse in a real-world horse race at a licensed racetrack to a virtual racer (avatar) in a simulated event. In all games described herein, the simulated event can comprise any type of race or other event including vehicle races, other animal races, or other desired contested events. In some embodiments, when a consumer selects a wager in the type 1 game, the system is configured to place the same wager on the corresponding runner or participant in the matched real-world race. In some embodiments, the system is configured to retrieve the official results when the real-world race is completed. In some embodiments, the system is configured to display the outcome of the real-world race in the same order the real-world live horse race was finished. In some embodiments, if the consumer picked the winner of the matched real-world race, the selection wins in the type 1 virtual race game. In some embodiments, the type 1 virtual race game includes a different visual display of the outcome of a real-world horse race.

In some embodiments, for type 2 style games, the system is configured to enable consumers to select a "quick pick" and/or select a series of numbers (e.g., four to six numbers). In either case, the system is configured to match the number series to runners or other participants in a single real-world horse race or the same number of consecutive races at a real-world racetrack according to some embodiments.

In some embodiments, type 3 games, sometimes called package games, the system is configured to enable a user to select a game package at a specified price. In some embodiments, purchase of a game package configures the system to make a selection of wagers on one or more real-world races utilizing proprietary algorithms.

In some embodiments, in all game types, results of real-world wagers (e.g., pari-mutuel) placed through the system are revealed to consumers when the users play the game that they selected. With Type 2 and Type 3 games, the system is configured to determine the wagers to be placed, enable wagers to be approved by the user, and/or implement various factors described herein in selecting which race to wager upon and which wager types to utilize.

In some embodiments, the system is configured to use one or more of the following factors when determining and/or selecting the real-world race and/or type of wager to be placed:

(1) When the upcoming live races are scheduled to run, as the goal is to provide an outcome of the wager as soon as possible, subject to balancing this objective with the other factors according to some embodiments.

(2) Which bet types are available for wagering in upcoming races, as different bet types have different takeout rates (the amount held from the pool of all wagers before distributing the balance of the pool to players making the winning selection) which dictates how much is returned to consumers according to some embodiments. In some embodiments, the system is configured to factor in takeout rates to maximize winnings to the consumer.

(3) The winning odds on the different runners in the upcoming races according to some embodiments. In some embodiments, winning odds are an important factor because different odds result in different winning payouts, which dictate how much is returned to consumers.

(4) The amount of money bet in the different wagering pools for each runner in the upcoming races according to some embodiments. In some embodiments, larger pool amounts can help stabilize the ability to better predict the final odds when all monies are wagered. In addition, in some embodiments, the system is configured to use the pool amounts for some bet types in some instances to help predict the likely winning runners or other participants, maximizing winnings to the user.

(5) The host track fee on the upcoming races, which is the percent of the wager paid to the track where the race is run according to some embodiments. In some embodiments, host track fees have a direct impact on the cost of the wager and thus the profitability of placing the wager.

(6) Any source market fees on the upcoming races which may be incurred in placing a wager on a track, which is principally determined by the consumer's physical location or legal residence according to some embodiments. In some embodiments, source market fees have a direct impact on the cost of the wager and thus the profitability of placing the wager. In some embodiments, the system is configured to use one or more conventional geolocation techniques to determine the user's location and/or the location where the real-world event bet is being placed. In some embodiments, the system is configured to enable a user to input one or more legal documents into the system to verify residence (e.g., scan driver's license).

(7) The state taxes and fees on upcoming races which are imposed on wagers on the upcoming races according to some embodiments. In some embodiments, state taxes and fees have a direct impact on the cost and thus the profitability of placing the wager. In some embodiments, some state taxes and fees are dictated by where the consumer resides, but some are dictated by the location of the track where the wager is placed.

(8) Any prioritization of particular tracks, as when contractual or regulatory accommodations result in favoring a particular track or group of tracks over other available tracks, based on the residence of the consumer and/or other factors according to some embodiments.

Figure 5:
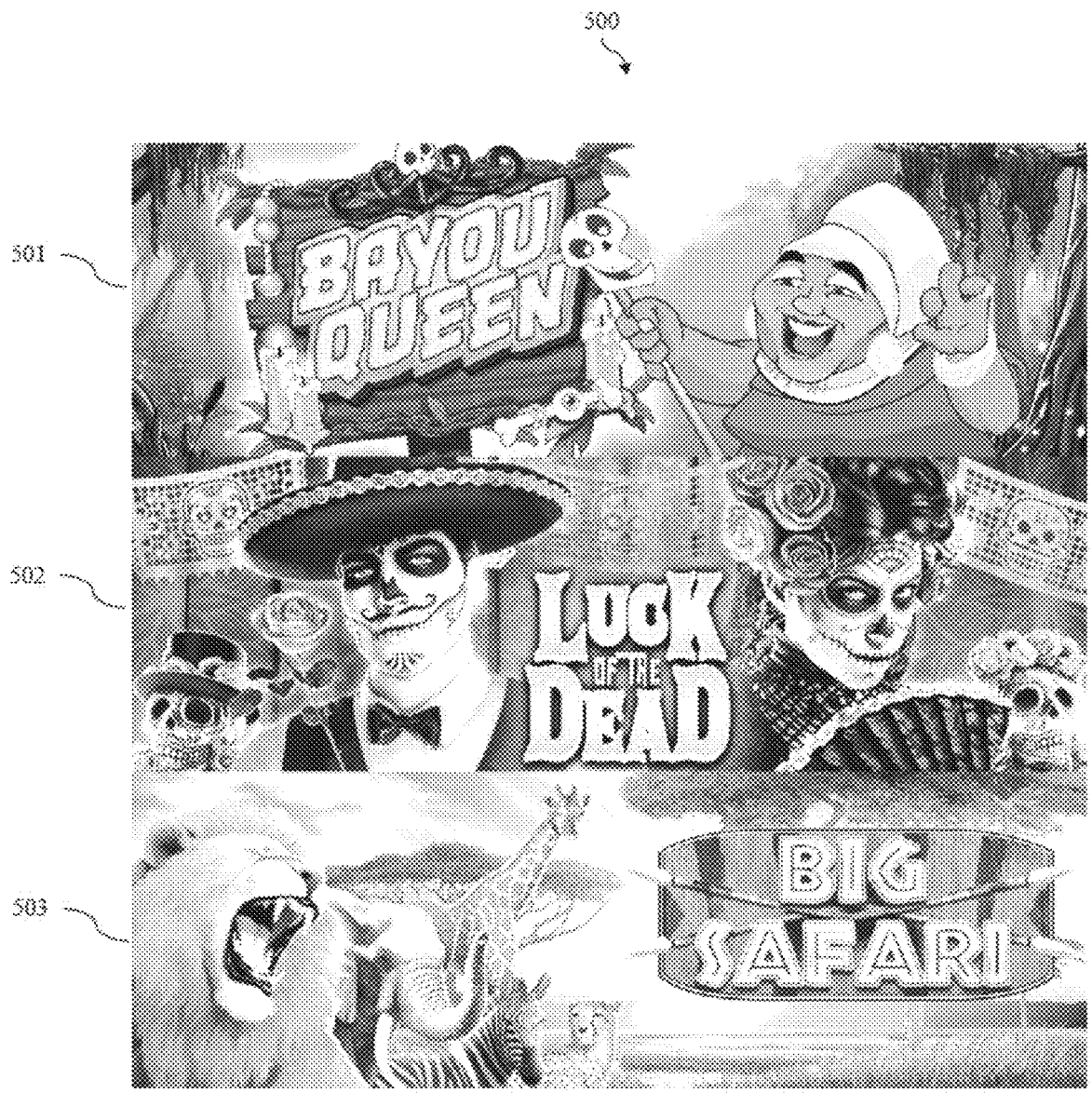
FIG. 5 depicts three game displays rendered by the system according to some embodiments.

FIG. 5 depicts three example game package displays rendered by the system according to some embodiments. In some embodiments, the game packages include Bayou Queen 501, Luck of the Dead 502, and Big Safari 503.

Some embodiments include Lottery Style Game Packages, referred to previously as type 2 games:

In some embodiments, the system is configured to utilize race wagers to create a "lottery" style game where customers can pick from multiple runners in a given race, or runners from multiple races, to create larger potential prizes for customers. In some embodiments, the system is configured to send the wagers placed by the customer in these games directly to the tote, with the outcomes of the game once again matching the dollar outcomes of the given wagers. In some embodiments, the Game Content Creation and Delivery module (GCCD) (see FIG. 1) for these games is configured to display to the customer a "lottery" style interface, whereby customers can pick a selection of numbers, along with a set dollar amount for their wager. In some embodiments, these picks are then configured to be converted into specific wagers by the system, where the system is configured to match the numbers chosen by the customer to the given pari-mutuel competitors for each wager. In some embodiments, total potential prize pools are configured to be displayed to the customer by the system to give the customer an idea of how much they may win. In some embodiments, after the customer places their wagers there may be hours and/or days between the time of their wagers and the outcome displayed to the customer. In some embodiments, the outcomes of the lottery style games are configured to match the outcome of the given pari-mutuel wagers by the system, which requires the customer to pick each number, in correct order, for their wagers to be winners.

In some embodiments, the system includes Keno Game Packages:

In some embodiments, the system is configured to display a Keno style game to the customers, whereby the system is configured to allow the customer will be able to pick (i.e., input via a graphical user interface) a predetermined set of numbers for a given cost per number, and/or a total cost for a set number of picks. In some embodiments, the GCCD system is configured to then algorithmically divide up the amount spent by the customer into a series, or individual, pari-mutuel bet(s) that are configured to drive the outcome of the game. In some embodiments, the determination of whether numbers chosen were "winning" numbers are configured by the system to be based on the results returned from the pari-mutuel bets. In some embodiments, if there are winnings from the pari-mutuel bets submitted, these dollar amounts will be converted into individual wins per number chosen by the system, with the aggregate amount won by the pari-mutuel wagers displayed across the given numbers chosen. In some embodiments, the display of the winning numbers to the customer will only commence after the outcome of the pari-mutuel wagers has been returned to the GCCD.

In some embodiments, the system includes Arcade Style Game Packages:

In some embodiments, the system is configured to enable customers to choose to place bets on competitors in a given arcade style game. In some embodiments, the system is configured to enable customers to choose which competitor and/or series of competitors will be the first ones to win or the last ones to lose in a given game. In some embodiments, prior to the display of the game outcome, the system is configured to take the amount spent by the customer on the game and then algorithmically divided the amount into pari-mutuel bets. In some embodiments, once the outcome of the pari-mutuel bets has been returned the GCCD system is configured to then determine the video display of the outcome of the given game and/or determine the standing of the competitors within the game based on the aggregate winning dollar value returned by the pari-mutuel bets. In some embodiments, the arcade style game is configured to then play out, with the finishing order of the competitors within the game presenting winnings to the customer that match the aggregate winnings of the pari-mutuel bets.

In some embodiments, the system includes Player Participant Game Packages:

In some embodiments, the system is configured to enable a customer to have the ability to have control of a given vehicle or animal within a preselected course. In some embodiments, the system is configured to enable the customer to control the movement of the vehicle, animal, and/or any other type of avatar through the course. In some embodiments, the system is configured to enable the customer to collect items that have a preset dollar value while controlling the movement of the avatar. In some embodiments, the system is configured to pay the customer a set amount for the amount of game play time and/or the number of potential items within the course. In some embodiments, the system is configured to use the amount paid for the given game to algorithmically determine a series of wagers that is configured to power the outcome of the game. In some embodiments, once the customer has purchased a game play the system is configured to wait until the results of the pari-mutuel bets have been returned. In some embodiments, the GCCD module is configured to then take the amount won from the pari-mutuel bets and divide this into amounts won for each package. In some embodiments, the system is configured to make the aggregate amount of all packages within a given course equal to the total amount won from the pari-mutuel wagers. In some embodiments, GCCD module is configured to then display the course and/or the number of packages and winnings for the customer to play within the game.

In some embodiments, the system includes Adventure Style Game Packages:

In some embodiments, the system is configured to enable a customer to have the ability to have control of a given character within a preselected environment. In some embodiments, the system is configured to enable the customer to maneuver the character (or any type of digital avatar) through the environment. In some embodiments, the system is configured to enable the character collecting items that have a preset dollar value. In some embodiments, the system is configured to enable the customer to pay a set amount for one or more of the amounts of game play time, the number of potential items within the course, or for a given number of game plays. In some embodiments the amount paid for the given game is used by the system to algorithmically determine a series of wagers that powers the outcome of the game. In some embodiments, once the customer has purchased a game play they the system is configured to wait until the results of the pari-mutuel bets have been returned. In some embodiments, the Game Content and Delivery module is configured to then take the amount won from the pari-mutuel bets and divide this into amounts won for each package collected. In some embodiments, the aggregate amount of all packages within the given environment is equal the total amount won from the pari-mutuel wagers. In some embodiments, the Game Content and Delivery module is configured to then present the environment and/or the number of packages and winnings for the customer to play within the game.

In some embodiments, the system includes Plinko Game Packages:

In some embodiments, the system is configured to execute and/or display a plinko style game to customers. In some embodiments, the system is configured to allow the customer to purchase a predetermined amount of plinko balls for a given cost per number. In some embodiments, the GCCD system is configured to then algorithmically divide up the amount spent by the customer into a series, or individual, pari-mutuel bet(s), the results of which will drive the outcome of the plinko game. In some embodiments, if there are winnings from the pari-mutuel bets submitted, these winnings will be converted into individual wins for each ball dropped within the plinko game, with the aggregate amount won by the pari-mutuel wagers displayed through the total balls dropped. In some embodiments, the GCCD is configured to display the winning outcomes, or replay the game play for the customer. In some embodiments, the system is configured to hold back a percentage of the purchase price of the tickets and use the held back percentage to make up part of the prize winnings of the balls played.

In some embodiments, the system includes Scratch and Win Game Packages:

In some embodiments, the system is configured to execute and/or display a scratch and win game to the user. In some embodiments, the system is configured to allow the customer to purchase a predetermined amount of scratch and win tickets for a given cost per ticket. In some embodiments, the GCCD system module is configured to algorithmically divide up the amount spent by the customer into a series, or individual, pari-mutuel bet(s)—the result of which will drive the outcome of the scratch and win game(s). In some embodiments, if there are winnings from the pari-mutuel bets submitted, the system is configured to convert these winnings into individual wins within each of the scratch and win tickets, with the aggregate amount won by the pari-mutuel bets displayed through the total scratch and win tickets purchased. In some embodiments, a percentage of the purchase price of the tickets will be held back to make up part of the prize winnings of the tickets purchased.

In some embodiments, the system includes a Wagering Tokens Game Play Mechanism:

In some embodiments, the system is configured to execute some games whereby the customer must purchase game wagering tokens in advance of play. In some embodiments, the PG is configured to use the money spent on purchasing the game tokens to place a wager (or series of wagers) into the live pari-mutuel pools. In some embodiments, the system is configured to place the wagers on historical pari-mutuel pools. In some embodiments, the system is configured to hold money from the purchase of the wagering tokens and give the customer the held money in the form of winnings within the game. In some embodiments, once the ET has provided the results of these wagers back to the GCCD, the customer can then use their wager tokens to play games. In some embodiments, the game wagering tokens are not redeemable for any use other than for playing the games, but once the customer has purchased these wagering tokens they may play games repeatedly with these tokens.

In some embodiments, the system is configured to enable the customer to choose which game, and/or how many rounds of each game, they choose to play with their wagering tokens. In some embodiments, the system is configured to enable the customer to choose what denomination of game tokens they wish to wager with each round of game play. In some embodiments, the winnings from each game round are paid out in cash by the system, so while their wagering token wallet continues to diminish as they play the games, their cash wallet is increasing based on the winnings from their game play. In some embodiments, the system is configured to determine the cash winnings within the game play by the outcome of the wagers previously placed by the PG during the initial purchase of the wagering tokens. In some embodiments, the winning outcome within the games is from the initial money spent to purchase wagering tokens. In some embodiments, once the customers wagering balance reaches zero the customer must purchase additional tokens in order to play additional games.

In some embodiments, the system includes one or more Contests:

In some embodiments, contests are both for paying customers (meaning a user which has deposited and wagered a certain amount prior to entering) or free (anyone can enter). In some embodiments, the system is configured to enable a user to check their eligibility to play the given contests, then make their picks for which runners will come in 1st, 2nd & 3rd. In some embodiments, the system is configured to take all the picks and those runners with the most picks for each position, and place wagers on behalf of the user. In some embodiments, the system is configured to distribute the winnings from those wagers amongst all participants.

In some embodiments, users are able to enter contests whereby the user, either for free and/or with some pre-selected eligibility requirements, can pick the winners for a pre-selected race, where the system aggregates the picks of all the users in the given contest, and the system then makes wager selections based on the aggregate decision of the contest participants (i.e., a group of users). In some embodiments, the system is configured to then place those wagers on behalf of the contest participants, and then distribute any winnings from those wagers equally amongst the contest participants. In some embodiments, the system is configured to "weight" the user picks differently based on the success or failure of the user's previous picks.

In some embodiments, the system is configured to display those users that successfully picked the correct winners for the race, even if the picks were not the ones placed by the system, in order to recognize those users who successfully made the correct picks. In some embodiments, in the same fashion as with the virtual racing games (FIG. 1), the Potent Games Parimutuel Betting Platform (PG) is configured to send the user picks to the External Tote Betting System (ET) in order to place the wagers. In some embodiments, the system is configured to send the results of those wagers back to the PG from the ET. In some embodiments, once the results have been received, the Game Content Creation Delivery System (GCCD) is configured to then convert the results of the event into the virtual sport display for final screens, as well as display the final results and payouts of all wagers, whether won or lost, identifying any wagers that won and the total amount won.

In some embodiments, the system includes a Historical Racing Outcome Engine:

In some embodiments, the system is configured to enable wagers on live races to be replaced by wagers on historical (pari-mutuel) races. In some embodiments, the outcomes from these historical races are configured to drive the outcomes for the given virtual racing game or game package by the system. In some embodiments, the algorithmic or direct wagers placed are configured by the system to be done in the same manner as with the live races. In some embodiments, the wagers will alternatively be placed on the outcome of an historical pari-mutuel races by the system as opposed to live races. In some embodiments, the system is configured to enable the outcomes of these historical races to be much faster than those of live races. In some embodiments, historical races do not require any waiting period by the customer for any of the games presented herein.

Figure 6:
FIG. 6 depicts a graphical user interface in which the user sees upcoming races for the variety of virtual sports offered according to some embodiments.

FIG. 6 depicts a graphical user interface in which the user sees upcoming races for the variety of virtual sports offered according to some embodiments. In some embodiments, the system is configured to enable customers to see one or more of a given sport, minimum bet amounts, size of the win pool, and when the race is about to start. In some embodiments, the system is configured to pass this information from the External Tote Betting System through to the Potent Games Parimutuel Betting Platform.

Figure 7:
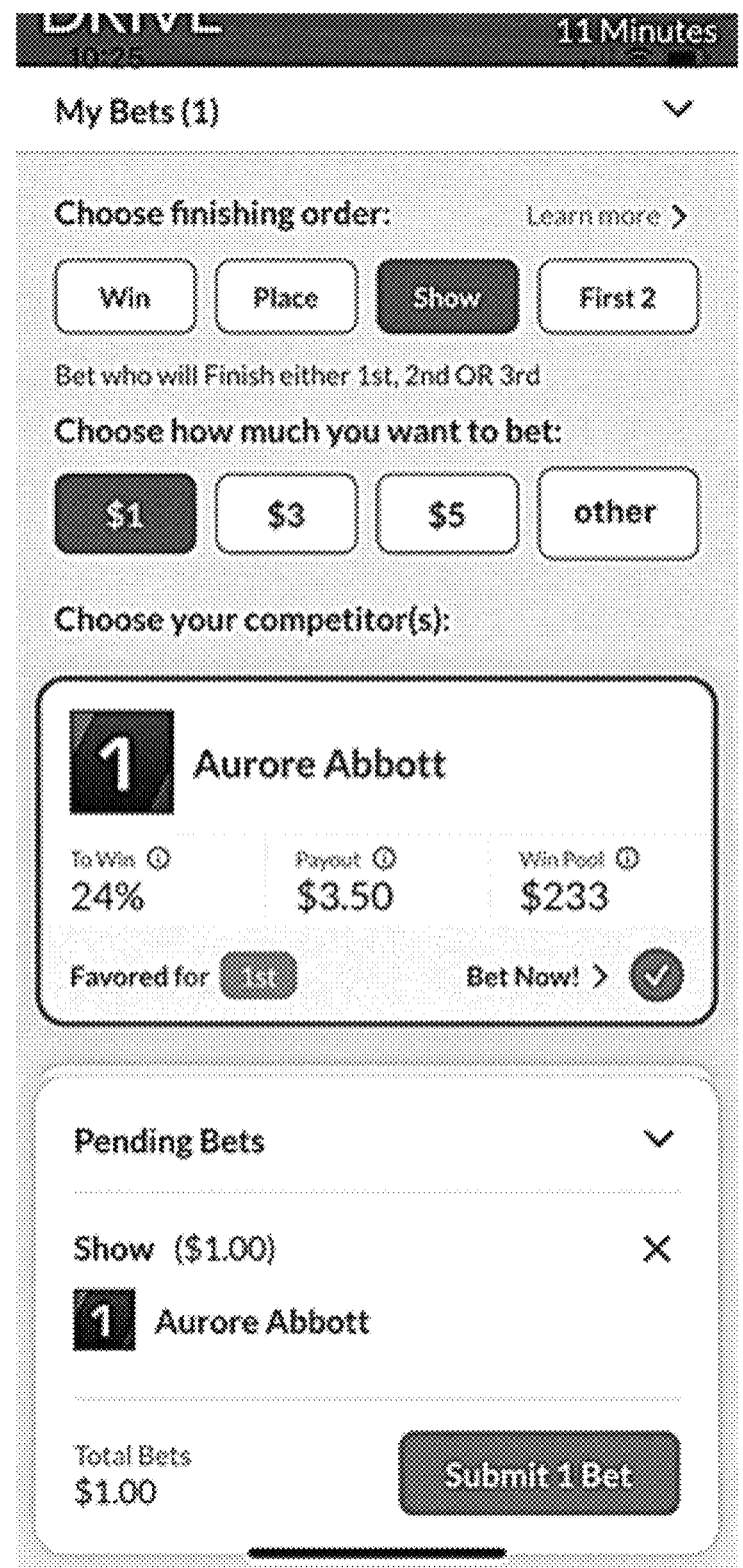
FIG. 7 depicts the graphical user interface that the customer sees for placing their wagers according to some embodiments.

FIG. 7 depicts the graphical user interface that the customer sees for placing their wagers according to some embodiments. In some embodiments, one or more of the "To Win" odds, "Approx Payout," "Win Pool," amounts, bet types and minimum bet amounts are derived directly from the External Tote Betting System that is providing these details from the given live race that the virtual race has been matched up with. In some embodiments, when a user places a bet on the virtual race through the interface in FIG. 7, the wager is sent by the Potent Games Parimutuel betting platform to the External Tote Betting System, and "comingled" with the given track & race real event that the virtual race simulated event that the wager has been matched up with.

Figure 8:
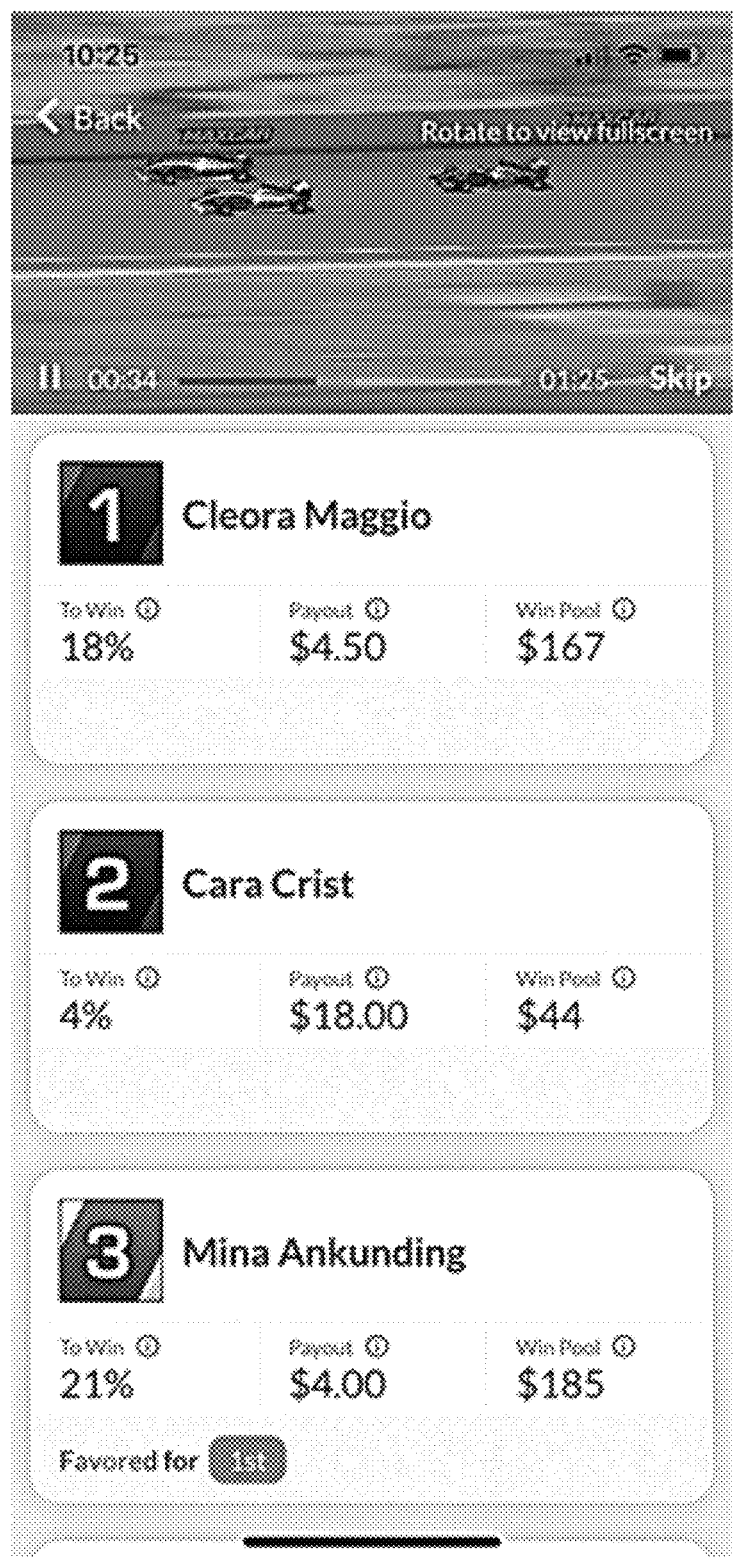
FIG. 8 show a graphic user interface of what the customer sees after the External Tote Betting System has provided the results to the Potent Games Parimutuel Betting Platform according to some embodiments.

FIG. 8 show a graphic user interface of what the customer sees after the External Tote Betting System has provided the results to the Potent Games Parimutuel Betting Platform according to some embodiments. In some embodiments, the Game Content Delivery System is configured to convert the results of the real event into a virtual sports display, display the simulated event, and display the outcome of the finishing order of the simulated event matching that of the real event the simulated event was initially matched up with.

Figure 9:
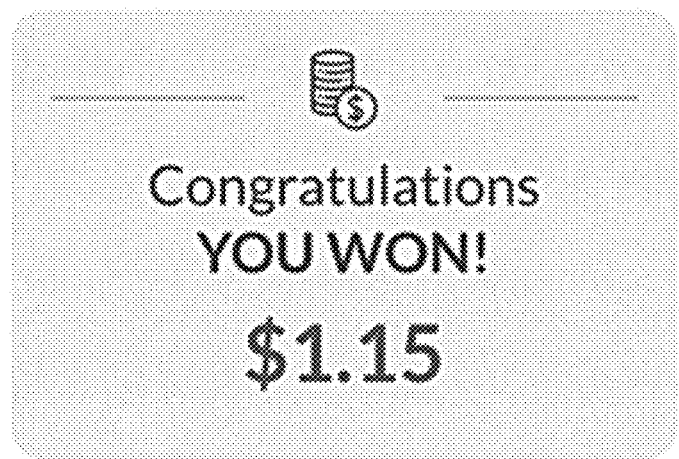
FIG. 9 shows a graphical user interface displaying the results of a customer virtual sporting event according to some embodiments.
Figure 9:
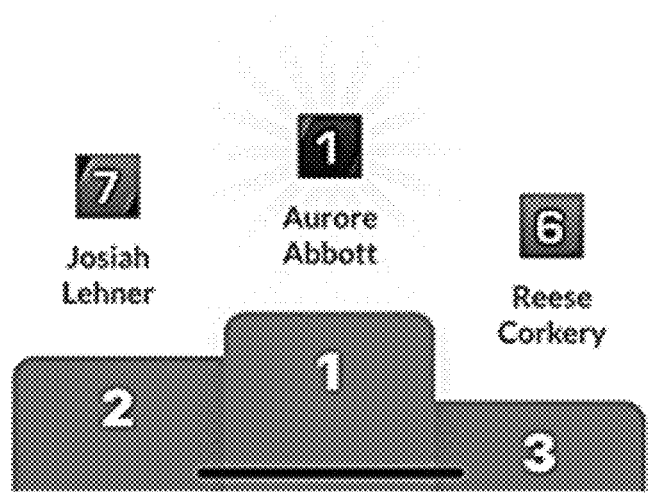
Figure 10:
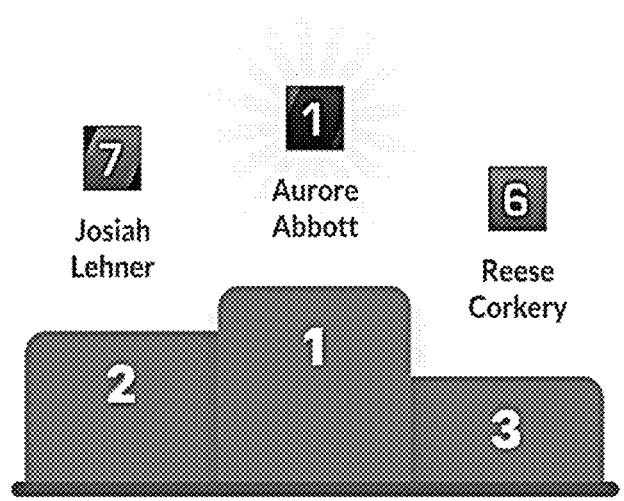
FIG. 10 shows another graphical user interface displaying a results of the customer virtual sporting event according to some embodiments.

FIGS. 9 and 10 show a graphical user interfaces displaying the results of a customer virtual sporting event according to some embodiments. In some embodiments, the system is configured to match the outcome of the virtual sporting event (simulated event) with the outcome of the real event that the simulated event was matched with. In some embodiments, the system is configure to add additional marketing promotional monies to the amounts wager outcome amounts, wherein the additional promotional monies increase the total monies going to the player. In some embodiments, all the wager payout amounts listed in the results area come from the External Tote Betting System which is configured to display the exact result of the real event that the simulated event is associated with.

Figure 11:
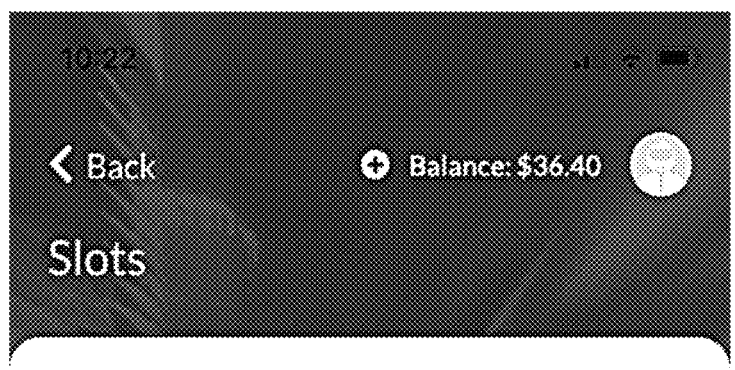
FIG. 11 depicts a GUI for a customer purchasing a single game pack according to some embodiments.
Figure 11:

FIG. 11 depicts a GUI for a customer purchasing a single game pack according to some embodiments. In some embodiments, the system is configured to enable the customer to choose a given game pack, for a specific price, that allows them a certain number of game plays (slot pulls, Match3 plays, Scratch and Win tickets, etc.)

Figure 12:
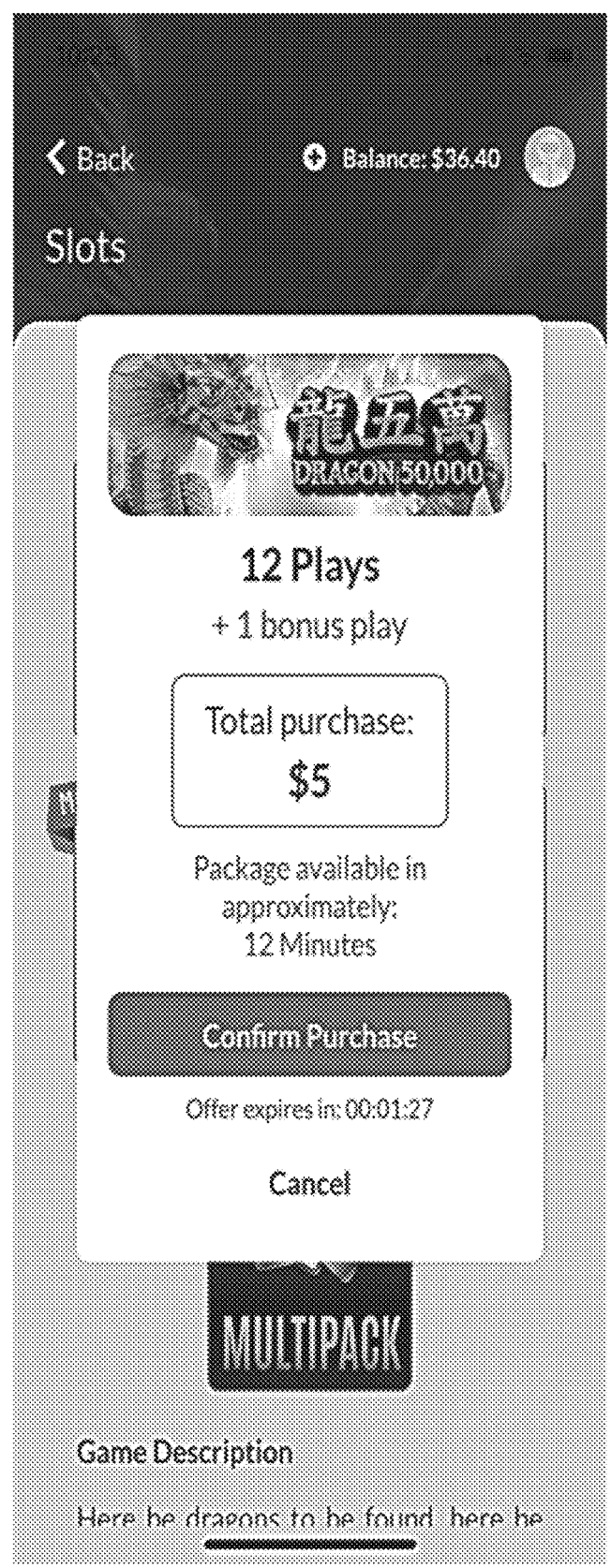
FIG. 12 illustrates a confirmation screen after a customer has chosen a given game pack according to some embodiments.

FIG. 12 illustrates a confirmation screen after a customer has chosen a given game pack according to some embodiments. In some embodiments, the FIG. 12 screen shows an approximate wait time before the customer will be able to play the game they have purchased. In some embodiments, the approximate wait time is based on the Potent Games Pari-mutuel betting engine reviewing the upcoming races and determining the next likely real event to wager on. In some embodiments, once the package is purchased, the Potent Games Pari-mutuel betting engine is configured to determine the type of wagers to be placed, and/or choose the appropriate next real event to place these wagers on.

Figure 13:
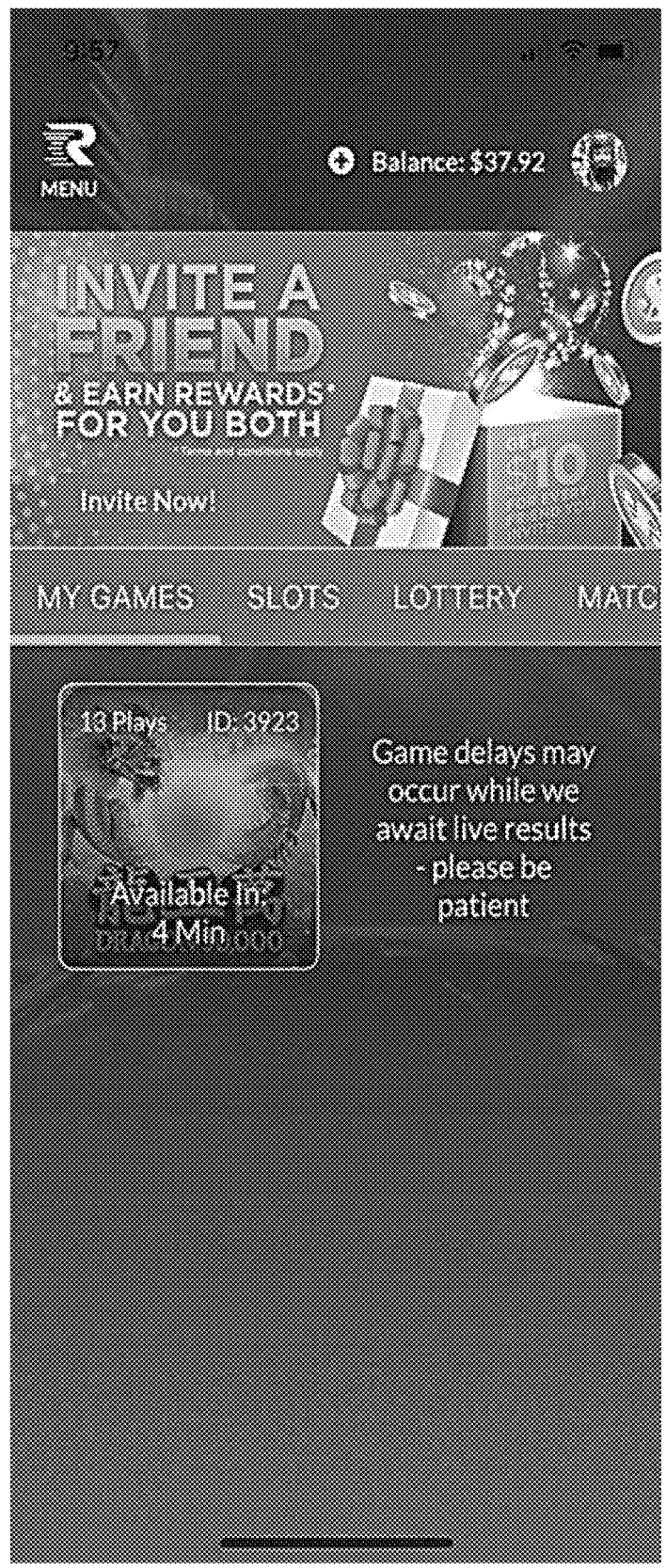
FIG. 13 depicts the purchased game pack being added to the players "My Games" area with a live countdown reflecting when the game pack will be available to play according to some embodiments.

FIG. 13 depicts the purchased game pack being added to the players "My Games" area with a live countdown reflecting when the game pack will be available to play according to some embodiments. In some embodiments, as the Game Content and Creation Delivery System gets updates from the Potent Games Pari-mutuel betting platform, based on the live information provided by the External Tote Betting system, the GCCD is configured to update the information on the game tile eventually resulting in a notification to the customer of the game being available to play and the tile displaying "Play Now!"

Figure 14:
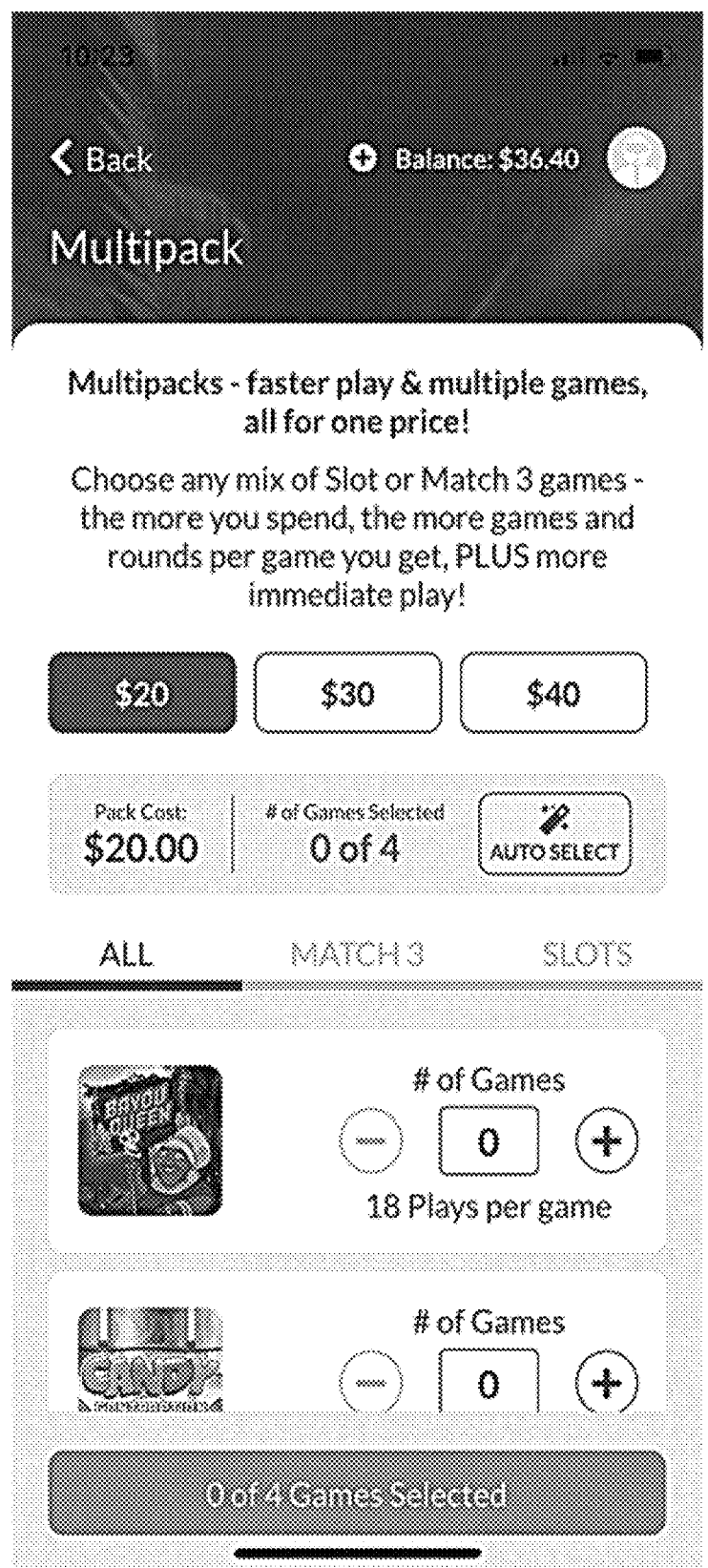
FIG. 14 illustrates an alternate purchasing option of game "Multipacks" according to some embodiments.

FIG. 14 illustrates an alternate purchasing option of game "Multipacks" according to some embodiments. In some embodiments, the system is configured to enable a user to purchase multiple game packs for a single price. In some embodiments, the system is configured to choose one or more games for the user to purchase for a single price. In some embodiments, the system is configured to enable the user to choose an "auto select" option whereby the system's algorithms choose the games for the user. In some embodiments, the "auto select" feature is configured to use at least a portion of a user's previous game play to algorithmically choose games based on the customers previous preferences. In some embodiments the "auto select" feature is configured to choose games based on the popularity of the game amongst users in the system database.

Figure 15:
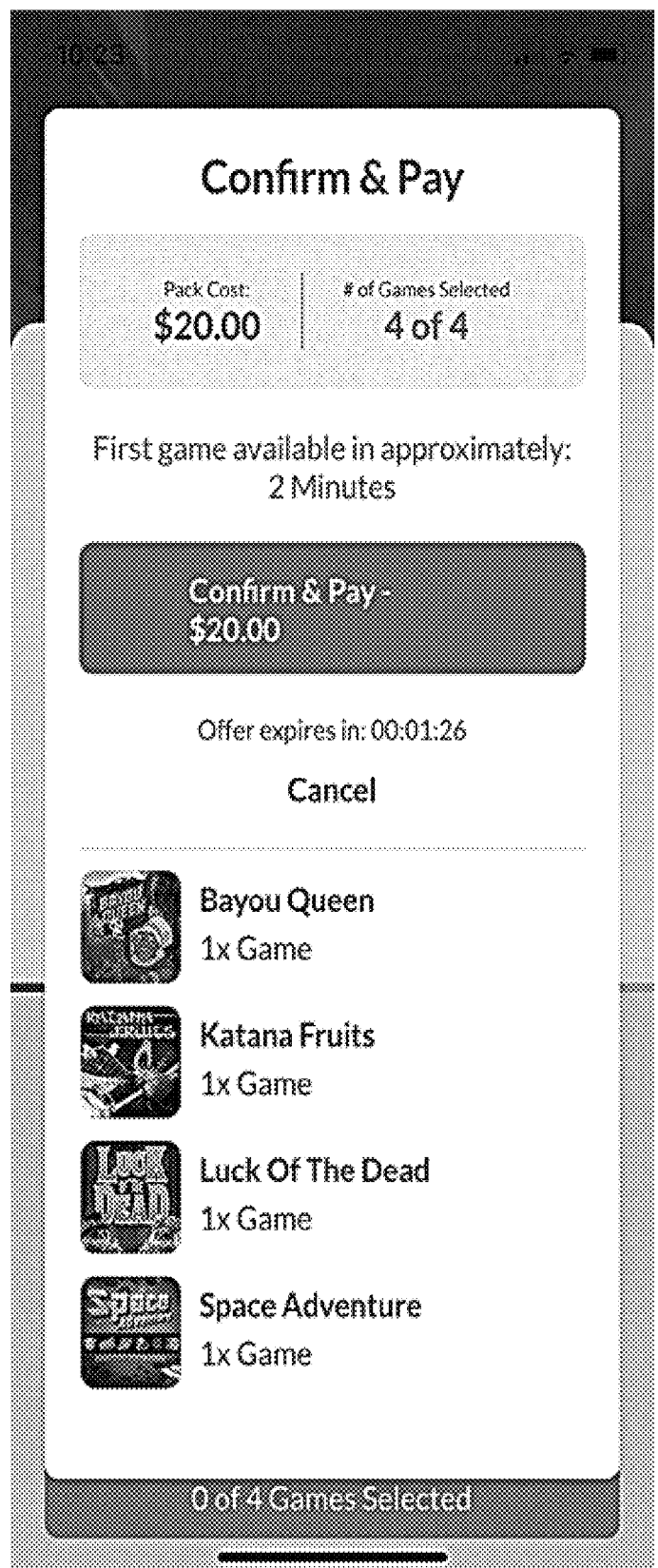
FIG. 15 represents the GUI that the customer will see after selecting the game packs in the "Multipack" option according to some embodiments.

FIG. 15 shows a GUI that the customer will see after selecting the game packs in the "Multipack" option according to some embodiments. In some embodiments, the system is configured to base the time displayed for the availability of the first pack on an upcoming real event, or alternatively an "artificial time." In some embodiments, the system is configured to allocated part of the purchase price of the original package to the winnings of a percentage of the purchased games. In some embodiments, the system the initial game does not require the outcome of the real event in order to display a "winning" amount due to the allocated part of the purchase price applied to the winnings.

Figure 16:
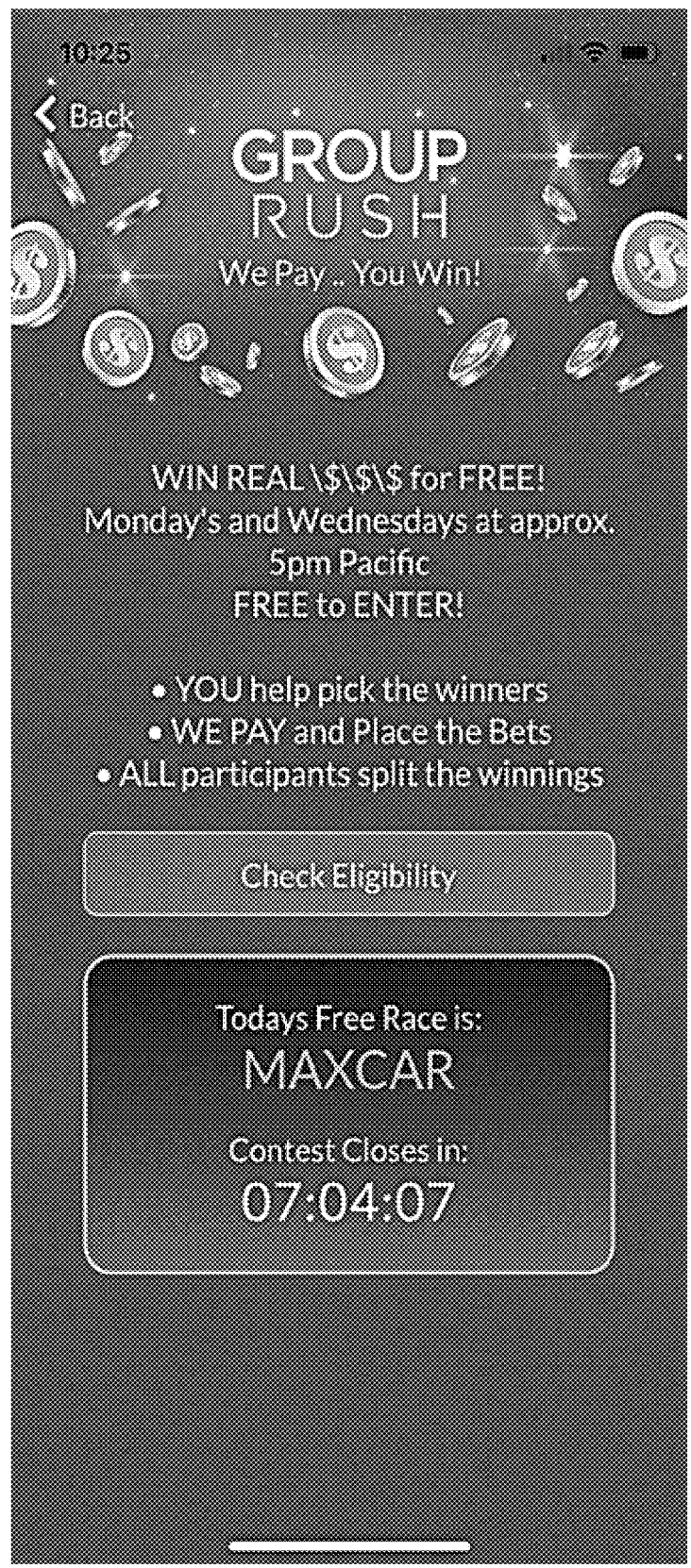
FIG. 16 shows a GUI that displays contest availability, the time that the contest closes, and the game type of the given contest according to some embodiments.

FIG. 16 shows a GUI that displays contest availability, the time that the contest closes, and the game type of the given contest according to some embodiments. In some embodiments, the system is configured to enable a user to check whether they are eligible for the contest (which is determined by the type of contest and the pre-chosen eligibility requirements of the given contest) using this GUI.

Figure 17:
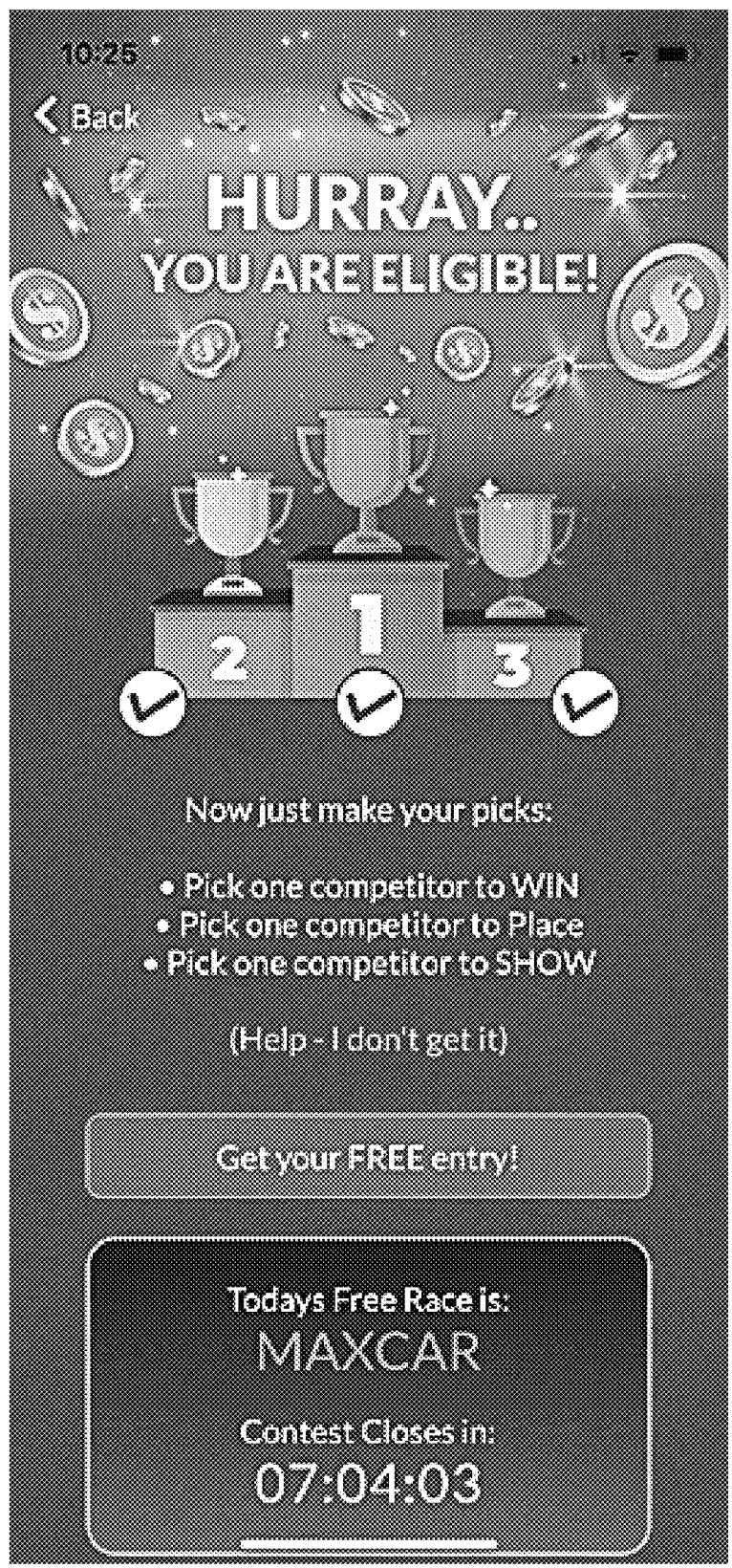
FIG. 17 depicts a GUI for a successfully eligible player outlining the requirements of the contest that the customer much complete in order to be eligible for the contest according to some embodiments.

FIG. 17 depicts a GUI for a successfully eligible player outlining the requirements of the contest that the customer much complete in order to be eligible for the contest according to some embodiments.

Figure 18:
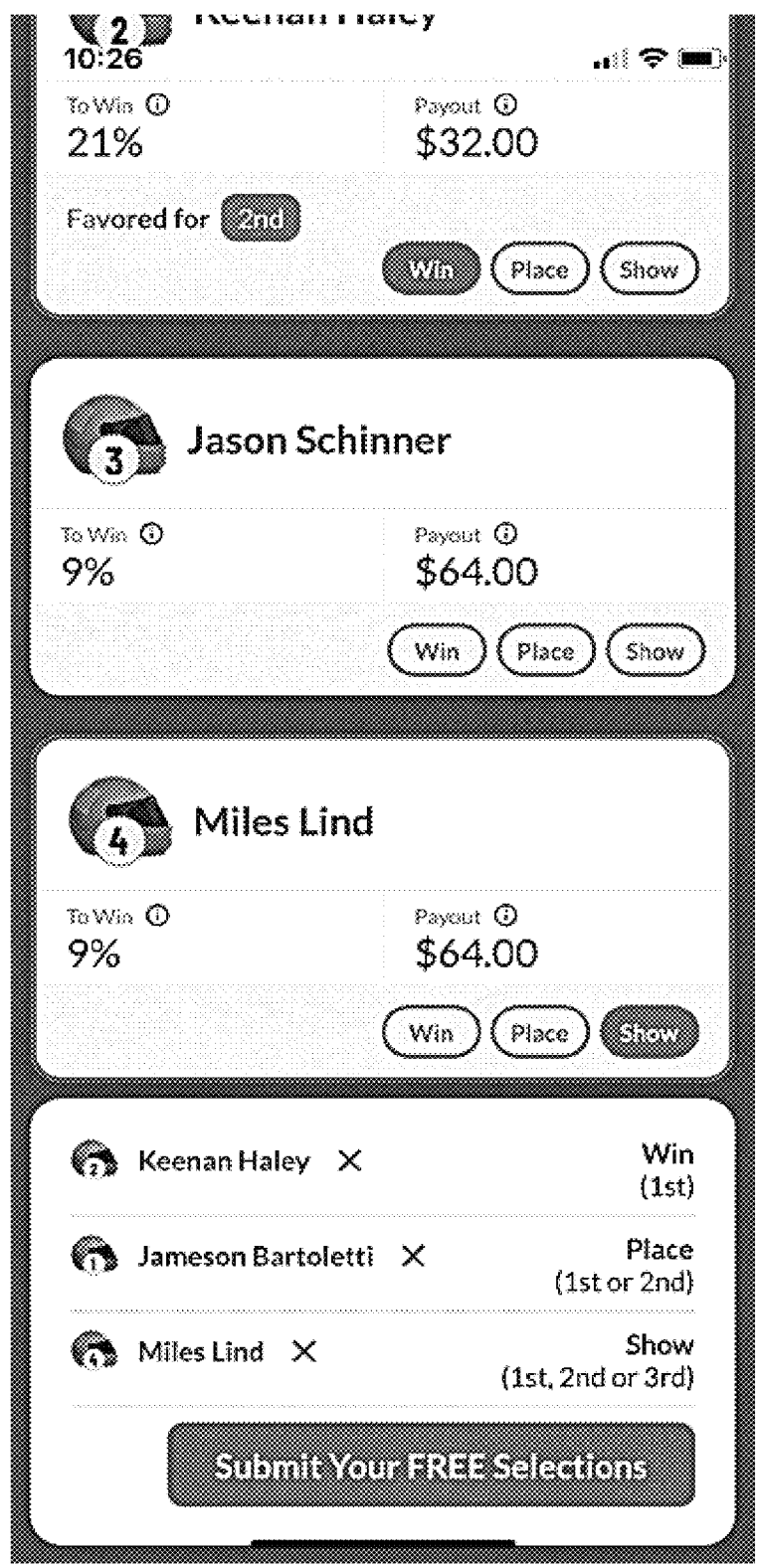
FIG. 18 shows a GUI used by the customer to make their selections in the contest according to some embodiments.

FIG. 18 shows a GUI used by the customer to make their selections in the contest according to some embodiments. In some embodiments, once the user makes their selections and submits them, they are now part of the real event and will get a split of the real event winnings.

Figure 19:
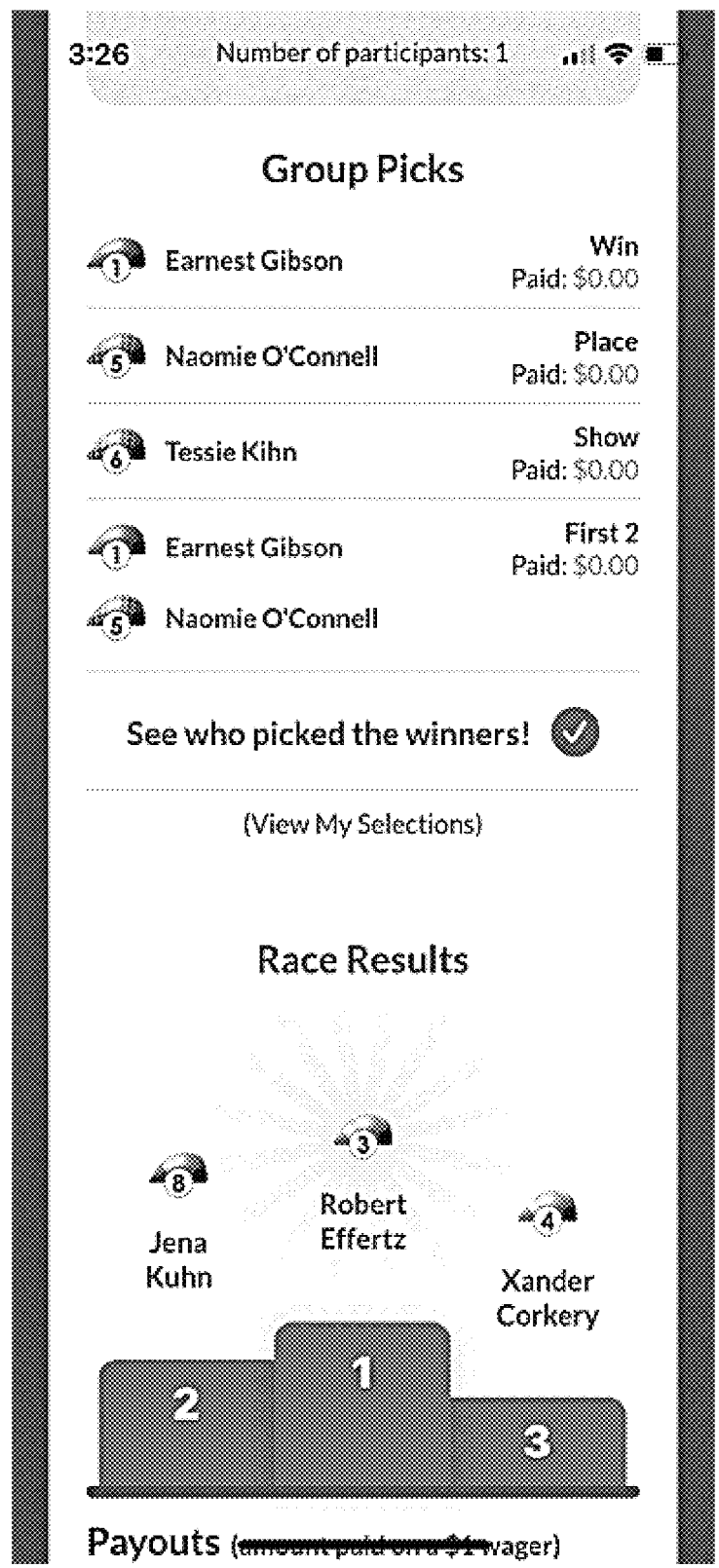
FIG. 19 illustrates aggregated group picks, and who were the top picks for each position according to some embodiments.

FIG. 19 illustrates aggregated group picks, and who were the top picks for each position according to some embodiments. In some embodiments, this GUI also gives the customer the ability to see who chose each pick correctly, even if none of the aggregated picks were winners.

Figure 20:
FIG. 20 illustrates a user interface for displaying the lottery style games according to some embodiments.

FIG. 20 illustrates a user interface for displaying the lottery style games according to some embodiments. In some embodiments, the system is configured to display one or more of lottery games available on the day of the lottery, lottery games available in advance, a countdown to when a lottery closes, and a type of lottery (e.g., pick 3, 4, 5, quick pick, etc.). In some embodiments, the system is configured to display games currently available for wagering.

Figure 21:
FIG. 21 depicts the UI in which the customer can make an individual selection for the given lottery game, or choose "quick pick" buttons of varying amounts in order to have the system assist in choosing the numbers based on the "favorites" of the given underlying race upon which the lottery is based according to some embodiments.

FIG. 21 depicts a GUI in which the customer can make an individual selection for the given lottery game, or choose "quick pick" buttons of varying amounts in order to have the system assist in choosing the numbers based on the "favorites" of the given underlying race upon which the lottery is based according to some embodiments. These "favorites" (where favorites means the runners at the given underlying race that customers have wagered the most money on, in order) are displayed to the customer as "hot numbers" to direct them to the numbers (runners) that have a higher likelihood of winning. In some embodiments, the system is configured to enable a user to make their selection, and then the system confirms their selection of numbers picked (e.g., either by themselves or through the quick pick automated selection).

Figure 22:
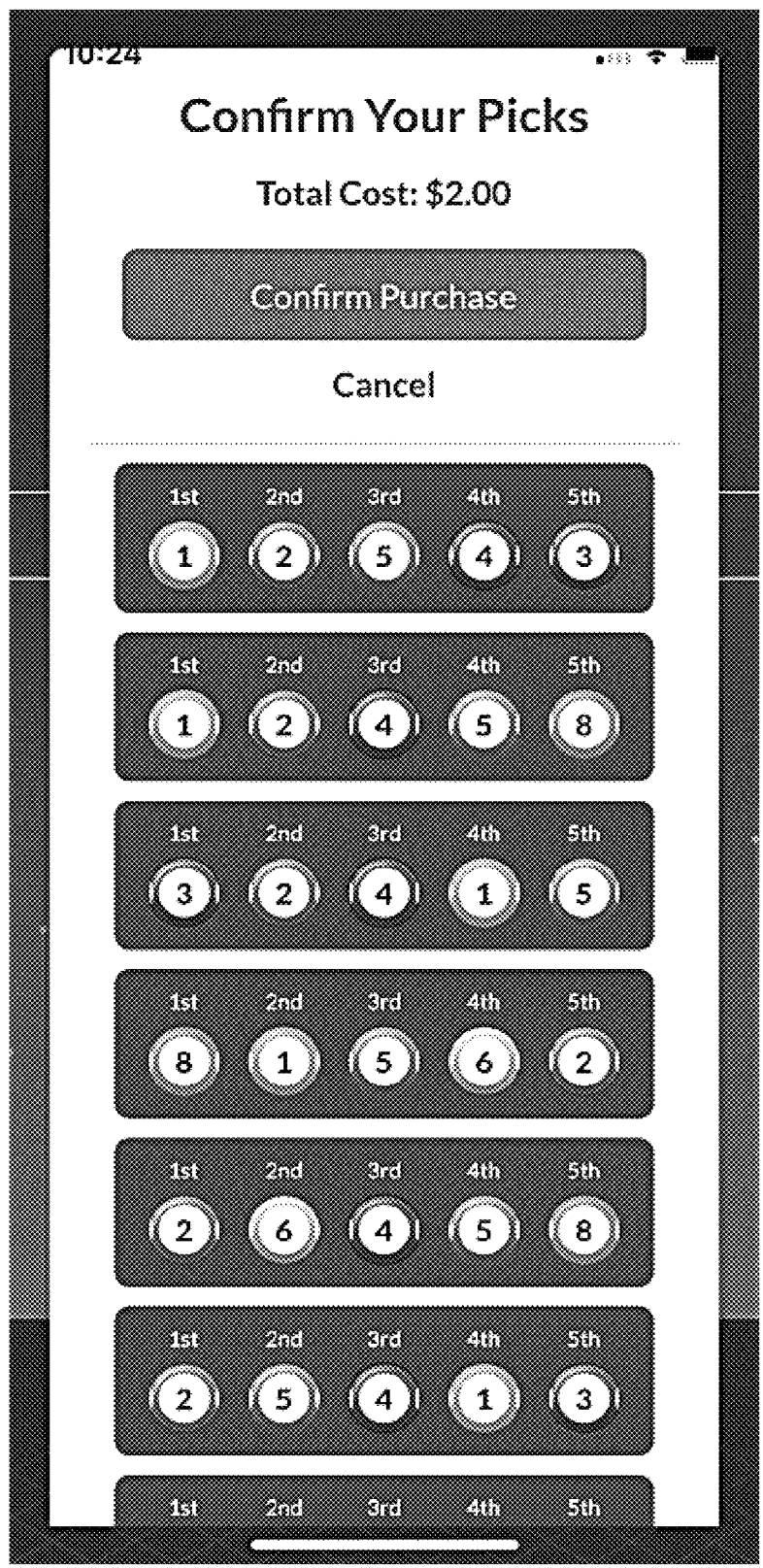
FIG. 22 shows a GUI for the confirmation of the customer picks of the lottery according to some embodiments.

FIG. 22 shows a GUI for the confirmation of the customer picks of the lottery according to some embodiments. In some embodiments, the GUI is configured to display a list of one or more picks made by the user or via the system through a quick pick selection.

Figure 23:
FIG. 23 illustrates a virtual ball "hopper" that displays the winning numbers from the lottery to the customer according to some embodiments.

FIG. 23 illustrates a virtual ball "hopper" that displays the winning numbers from the lottery to the customer according to some embodiments. In some embodiments, the "hopper" is configured to use the results that were provided to the PG from the ET and then the GCCD creates a virtual hopper to display the outcomes to the customer.

Figure 24:
FIG. 24 depicts a summary screen the customer sees after watching the virtual hopper, that summarizes the outcomes and lets the customer know the winning or losing outcome of their wager, and the amount they won (or would have won) according to some embodiments.

FIG. 24 depicts a summary screen the customer sees after watching the virtual hopper, that summarizes the outcomes and lets the customer know the winning or losing outcome of their wager, and the amount they won (or would have won) according to some embodiments.

It will be appreciated by those skilled in the art that while the system has been described above in connection with particular embodiments and examples, the system is not necessarily so limited, and that numerous other embodiments, examples, uses, modifications and departures from the embodiments, examples, and uses are intended to be encompassed by the description and figures attached hereto.

The subject matter described herein are directed to technological improvements to the field of virtual gambling and/or gaming. The disclosure describes the specifics of how a machine including one or more processors and one or more non-transitory computer implement the system and its improvements over the prior art. The instructions executed by the machine cannot be performed in the human mind or derived by a human using a pin and paper but require the machine to convert process input data to useful output data. Moreover, the claims presented herein do not attempt to tie-up a judicial exception with known conventional steps implemented by a general-purpose computer; nor do they attempt to tie-up an judicial exception by simply linking it to a technological field. Indeed, the systems and methods described herein provide a technologic improvement to the field of virtual gaming and/or gambling, and provides advantages not known in the prior art. Furthermore, the claimed system includes unconventional steps that confine the claim to a useful application.

Some embodiments of the system are presented with specific values and/or setpoints. These values and setpoints are not intended to be limiting and are merely examples of a higher configuration versus a lower configuration and are intended as an aid for those of ordinary skill to make and use the system. In addition, any system, game, or event described by a specific name is done for enablement purposes only and is not limiting in any way. Any of these terms may be replaced with their more generic designations when defining the metes and bounds of the system in order to afford the widest scope possible.

Furthermore, acting as Applicant's own lexicographer, Applicant imparts the explicit meaning and/or disavow of claim scope to the following terms:

Applicant defines any use of "and/or" such as, for example, "A and/or B," or "at least one of A and/or B" to mean element A alone, element B alone, or elements A and B together. In addition, a recitation of "at least one of A, B, and C," a recitation of "at least one of A, B, or C," or a recitation of "at least one of A, B, or C or any combination thereof" are each defined to mean element A alone, element B alone, element C alone, or any combination of elements A, B and C, such as AB, AC, BC, or ABC, for example.

"Substantially" and "approximately" when used in conjunction with a value encompass a difference of 5% or less of the same unit and/or scale of that being measured.

"Simultaneously" as used herein includes lag and/or latency times associated with a conventional and/or proprietary computer, such as processors and/or networks described herein attempting to process multiple types of data at the same time. "Simultaneously" also includes the time it takes for digital signals to transfer from one physical location to another, be it over a wireless and/or wired network, and/or within processor circuitry.

As used herein, "can" or "may" or derivations there of (e.g., the system display can show X) are used for descriptive purposes only and is understood to be synonymous and/or interchangeable with "configured to" (e.g., the computer is configured to execute instructions X) when defining the metes and bounds of the system.

In addition, the term "configured to" means that the limitations recited in the specification and/or the claims must be arranged in such a way to perform the recited function: "configured to" excludes structures in the art that are "capable of" being modified to perform the recited function but the disclosures associated with the art have no explicit teachings to do so. For example, a recitation of a "container configured to receive a fluid from structure X at an upper portion and deliver fluid from a lower portion to structure Y" is limited to systems where structure X, structure Y, and the container are all disclosed as arranged to perform the recited function. The recitation "configured to" excludes elements that may be "capable of" performing the recited function through modification but associated disclosures (or lack thereof) provide no teachings to make such a modification to meet the functional limitations between all structures recited. Another example is "a computer system configured to or programmed to execute a series of instructions X, Y, and Z." In this example, the instructions must be present on a non-transitory computer readable medium such that the computer system is "configured to" and/or "programmed to" execute the recited instructions: "configure to" and/or "programmed to" excludes art teaching computer systems with non-transitory computer readable media merely "capable of" having the recited instructions stored thereon but have no teachings of the instructions X, Y, and Z programmed and stored thereon. The recitation "configured to" can also be interpreted as synonymous with operatively connected when used in conjunction with physical structures.

It is understood that the phraseology and terminology used herein is for description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The previous detailed description is to be read with reference to the figures, in which like elements in different figures have like reference numerals. The figures, which are not necessarily to scale, depict some embodiments and are not intended to limit the scope of embodiments of the system.

Any of the operations described herein that form part of the system are useful machine operations. The system also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data is obtained over a network the data can be processed by other computers on the network, e.g. a cloud of computing resources.

The embodiments of the system can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, some embodiments include methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations are presented in a specific order according to some embodiments, the execution of those steps do not necessarily occur in the order listed unless a explicitly specified. Also, other housekeeping operations can be performed in between operations, operations can be adjusted so that they occur at slightly different times, and/or operations can be distributed in a system which allows the occurrence of the processing operations at various intervals associated with the processing, as long as the processing of the overlay operations are performed in the desired way and result in the desired system output.

It will be appreciated by those skilled in the art that while the system has been described above in connection with particular embodiments and examples, the system is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the system are set forth in the following claims.

We claim:

1. A system for virtual interactive sports comprising:
one or more computers comprising one or more processors and one or more non-transitory computer readable media, the one or more non-transitory computer readable media including instructions stored thereon that configure the one or more computers to implement:
a content module,
a platform betting module,
a display module, and
an external betting module;
wherein the platform betting module is configured to, by the one or more processors, send details of real events and betting opportunities to the content module;
wherein the system is configured to, by the one or more processors, transfer the details of the real events from the content module to the display module;
wherein the display module is configured to, by the one or more processors, display the details to a user;
wherein the display module is configured to, by the one or more processors, enable the user to make one or more betting selections;
wherein the content module is configured to, by the one or more processors, create one or more tickets based on the one or more betting selections;
wherein the content module is configured to, by the one or more processors, send the one or more tickets to the platform betting module;
wherein the platform betting module is configured to, by the one or more processors, send the one or more tickets to the external betting module;
wherein the external betting module is configured to, by the one or more processors, place one or more bets on one or more real events based on the one or more tickets;
wherein the content module is configured to convert the one or more real events associated with the one or more tickets into one or more simulated events for display by the display module; and
wherein the display module is configured to display the one or more simulated events to the user; and
wherein the one or more simulated events are in each instance a different type of event than each of the one or more real events.

2. The system of claim 1,
wherein the platform betting module is configured to receive results of the one or more real events associated with the one or more tickets
wherein the content module is configured to match an outcome of the one or more simulated events to the results of the one or more real events associated with the one or more tickets.

3. The system of claim 1,
wherein the one or more simulated events include one or more games.

4. The system of claim 3,
wherein the one or more games include one or more of a matching game, a ticket game, a lottery game, and a slot game.

5. The system of claim 1,
wherein the system is configured to allow the user to select one or more simulated event types before the one or more tickets are sent to the platform betting module.

6. The system of claim 5,
wherein the one or more simulated events include one or more virtual races.

7. The system of claim 1,
wherein the system is configured to enable the user to start the one or more simulated events before results of the one or more real events are known.

8. The system of claim 1,
wherein the system is configured to alter an outcome of the one or more simulated events once the system receives results of the one or more real events.

9. The system of claim 1,
wherein the system is configured to alter a position of avatars in the one or more simulated events based on the received results of the one or more real events.

10. The system of claim 1,
wherein each of the one or more simulated events includes one or more avatars;
wherein the one or more avatars each correspond to one or more competitors competing in the one or more real events.

11. The system of claim 2,
wherein each of the one or more simulated events include one or more avatars;
wherein the one or more avatars each correspond to one or more competitors competing in the one or more real events.

12. A system for virtual interactive sports comprising:
one or more computers comprising one or more processors and one or more non-transitory computer readable media, the one or more non-transitory computer readable media including instructions stored thereon that configure the one or more processors to implement:
a content module,
a platform betting module,
a display module, and
an external betting module;
wherein the platform betting module is configured to send details of upcoming live races and/or betting opportunities to the content module;
wherein the system is configured to transfer the details of the upcoming live races from the content module to the display module;
wherein the display module is configured to display the details to a user;
wherein the display module is configured to enable the user to make one or more betting selections;
wherein the content module is configured to create one or more tickets based on the one or more betting selections;
wherein the content module is configured to send the one or more tickets to the platform betting module;
wherein the platform betting module is configured to send the one or more tickets to the external betting module; and
wherein the external betting module is configured to place one or more bets on one or more live races based on the one or more tickets;
wherein the system is configured to represent one or more competitors from the one or more live races as avatars in one or more virtual races;

wherein the content module is configured to convert the one or more live races associated with the one or more tickets into one or more virtual races for display by the display module; and wherein the display module is configured to display the one or more virtual races to the user; and wherein the one or more virtual races are each a different type of race than each of the one or more live races.

13. The system of claim 12, wherein the one or more live races are chosen by the system at random or in accordance with rules for selecting live races by the platform betting module.

14. The system of claim 12, wherein the one or more live races are chosen by the system based on a start time for each of the one or more live races.

15. The system of claim 12, wherein at least one of the one or more virtual races includes two or more rounds.

16. The system of claim 15, wherein each of the two or more rounds correspond to a different one of the one or more live races.

17. The system of claim 12, wherein the platform betting module is configured to receive results of the one or more live races associated with the one or more tickets;

wherein the content module converts the results of the one or more live races associated with the one or more tickets into the one or more virtual races for display by the display module; and wherein the display module is configured to display the one or more virtual races to the user.

18. The system of claim 8, wherein the system is configured to allow the user to start the one or more virtual races before the results of the one or more live races are known.

19. The system of claim 18, wherein the system is configured to alter one or more competitor positions in the one or more virtual races once the system receives the results of the one or more live races.

\* \* \* \* \*